United States Patent
Lopez et al.

(10) Patent No.: US 12,398,206 B2
(45) Date of Patent: Aug. 26, 2025

(54) ANTIBODIES HAVING SPECIFICITY FOR NECTIN-4 AND USES THEREOF

(71) Applicants: UNIVERSITÉ D'AIXMARSEILLE, Marseilles (FR); INSERM (INSTITUT NATIONAL DE LA SANTÉ ET DE LA RECHERCHE MÉDICALE), Paris (FR); INSTITUT JEAN PAOLI & IRENE CALMETTES, Marseilles (FR); CENTRE NATIONAL DE LA RECHERCHE SCIENTIFIQUE—CNRS -, Paris (FR)

(72) Inventors: Marc Lopez, Marseilles (FR); Daniel Olive, Marseilles (FR)

(73) Assignees: UNIVERSITÉ D'AIXMARSEILLE, Marseilles (FR); INSERM (INSTITUT NATIONAL DE LA SANTÉ ET DE LA RECHERCHE MÉDICALE, Paris (FR); INSTITUT JEAN PAOLI & IRENE CALMETTES, Marseilles (FR); CENTRE NATIONAL DE LA RECHERCHE SCIENTIFIQUE—CNRS, Paris (FR)

(*) Notice: Subject to any disclaimer, the term of this patent is extended or adjusted under 35 U.S.C. 154(b) by 812 days.

(21) Appl. No.: 17/766,597

(22) PCT Filed: Oct. 7, 2020

(86) PCT No.: PCT/EP2020/078146
§ 371 (c)(1),
(2) Date: Apr. 5, 2022

(87) PCT Pub. No.: WO2021/069508
PCT Pub. Date: Apr. 15, 2021

(65) Prior Publication Data
US 2023/0183337 A1 Jun. 15, 2023

(30) Foreign Application Priority Data
Oct. 7, 2019 (EP) .................... 19306306

(51) Int. Cl.
C07K 16/28 (2006.01)
A61K 39/00 (2006.01)
A61P 35/00 (2006.01)
A61P 35/04 (2006.01)
A61K 47/68 (2017.01)

(52) U.S. Cl.
CPC .............. *C07K 16/28* (2013.01); *A61P 35/00* (2018.01); *C07K 2317/24* (2013.01); *C07K 2317/565* (2013.01)

(58) Field of Classification Search
CPC ..................... C07K 16/28; A61K 2039/505
See application file for complete search history.

(56) References Cited

U.S. PATENT DOCUMENTS

2018/0243434 A1* 8/2018 Lopez ............... A61K 47/6801

FOREIGN PATENT DOCUMENTS

WO 2018/226578 A1 12/2018

OTHER PUBLICATIONS

Buchwalow et al. Scientific Reports. 1: 28; Published: Jul. 1, 2011 (Year: 2011).*
Nishiwada et al. Journal of Experimental & Clinical Cancer Research. 34 (1): 30; Published: Mar. 28, 2015 (Year: 2015).*
Merriam-Webster. Definition of Of. Accessed: Apr. 21, 2025 (Year: 2025).*
M-Rabet et al. Annals of Oncology. 28: 769-776; Published: Dec. 2016 (Year: 2016).*
Fabre-Lafay et al. Journal of Biological Chemistry. 280 (20): 19553-19550; Published: May 20, 2005 (Year: 2005).*
Bekos et al. Cancers. 11 (5): 698; Published: May 20, 2019 (Year: 2019).*
Alfarouk et al. Cancer Cell International. 15: 71; Published: Jul. 15, 2015 (Year: 2015).*
Loganzo et al. Molecular Cancer Therapeutics. 15 (12): 2825-2834; Published: Dec. 1, 2016 (Year: 2016).*
Collins et al. Cancers. 11 (3): 394; Published: Mar. 20, 2019 (Year: 2019).*
Nishiwada et al: "Nectin-4 expression contributes to tumor proliferation, angiogenesis and patient prognosis in human pancreatic cancer", Journal of Experimental & Clinical Cancer Research, vol. 34, No. 1, Mar. 28, 2015.
Takano et al: "Identification of Nectin-4 Oncoprotein as a Diagnostic and Therapeutic Target for Lung Cancer", Cancer Research, vol. 69, No. 16, p. 6694-6703, Aug. 15, 2009.

* cited by examiner

*Primary Examiner* — Janet L Epps-Smith
*Assistant Examiner* — Katherine Ann Holtzman
(74) *Attorney, Agent, or Firm* — M. Scott McBride

(57) ABSTRACT

The present invention relates to antibodies having specificity for Nectin-4 and uses thereof, in particular for the treatment of cancer.

Figure 1:
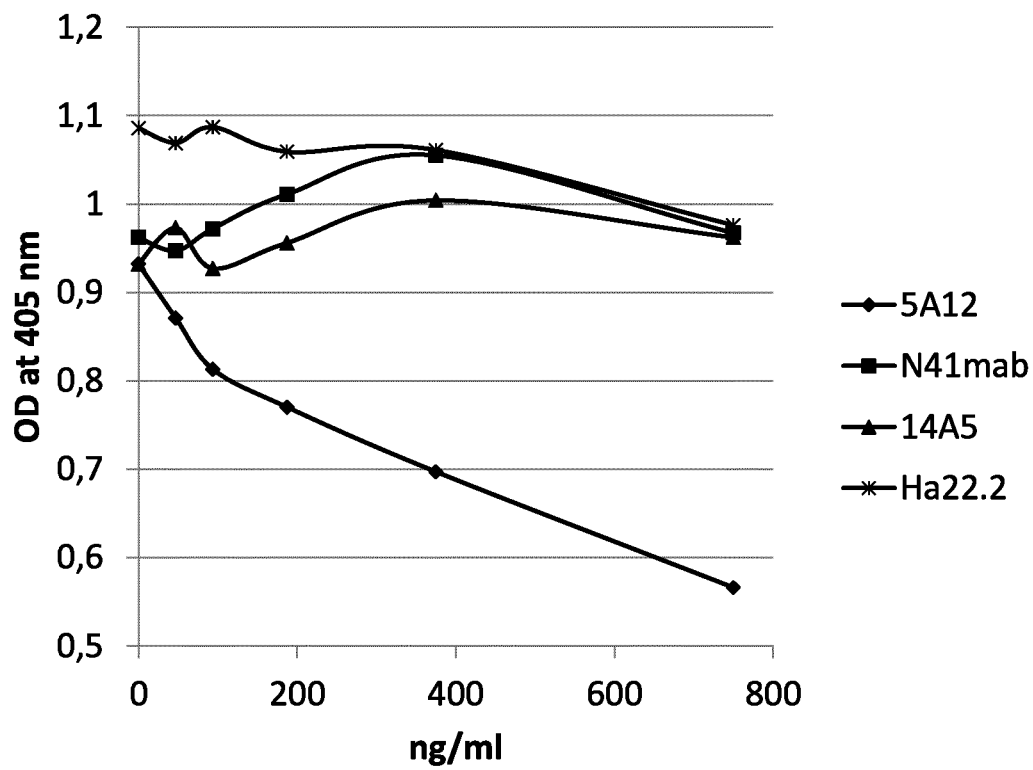

20 Claims, 4 Drawing Sheets
Specification includes a Sequence Listing.

A

B

| Mab | EC50 (ng/ml) | F-Max |
|---|---|---|
| N41 | 52 | 69944 |
| 14A5 | 34 | 73683 |
| 5A12 | 18 | 119145 |

| Mab | IC50 (ng/ml) |
|---|---|
| N41 | 7.58 |
| 14A5 | 6.36 |
| 5A12 | 1.82 |

ANTIBODIES HAVING SPECIFICITY FOR NECTIN-4 AND USES THEREOF

FIELD OF THE INVENTION

The present invention relates to antibodies having specificity for Nectin-4 and uses thereof.

BACKGROUND

Nectin-4 is a surface molecule that belongs to the nectin family of proteins, which comprises 4 members. Nectins are cell adhesion molecules that play a key role in various biological processes such as polarity, proliferation, differentiation, and migration, for epithelial, endothelial, immune, and neuronal cells, during development and adult life. They are involved in several pathological processes in humans. They are the main receptors for poliovirus, herpes simplex virus and measles virus.

PVRL4/Nectin-4 is involved in the formation and maintenance of adherens junctions in cooperation with cadherins. Indeed, Nectin-4 is a type I transmembrane cell adhesion molecule composed of three Ig-like domains (V-C-C type) in its extracellular region. It is also a receptor for the measles virus, mediating its endocytosis. Nectin-4 is expressed during foetal development, with expression declining in adult life by contrast with the extensive expression of the other nectins in adult tissues.

It has been shown (see references 1, 2, 3, 4, 5, 6) that nectin-4 is re-expressed as a tumour-associated antigen with pro-oncogenic properties in various carcinomas including breast cancer. In particular, Nectin-4 is a tumor-associated antigen in 50%, 49% and 86% of breast, ovarian and lung carcinomas, respectively, mostly on tumors of bad prognosis. In breast tumors, Nectin-4 is expressed mainly in triple-negative and ERBB2+ carcinomas. In the serum of patients with these cancers, the detection of soluble forms of Nectin-4 is associated with a poor prognosis. Levels of serum Nectin-4 increase during metastatic progression and decrease after treatment.

These features associated with its limited expression in the respective normal tissues, suggest that nectin-4 could be a relevant therapeutic target for antibody-drug conjugate (ADC) in these cancers, as recently reported in bladder, breast and pancreatic cancers (refs. 5, 6).

Accordingly, several anti-Nectin-4 antibodies have been described in the prior art. In particular, EnfortumabVedotin (ASG-22ME, e.g., Ha22-2 mAb from Seattle Genetics) is an antibody-drug conjugate (ADC) targeting Nectin-4 and is currently clinically investigated for the treatment of patients suffering from solid tumors.

WO2017042210 and WO2018158398 also provided anti-Nectin-4 antibodies (i.e., N41 mAb and 14A5.2 mAb, which recognize with a similar affinity, an epitope different from the epitope recognizes by the Ha22-2 antibody and are useful for the treatment of cancer.

However, these antibodies are only intended to be used for therapeutic application. Indeed, none of them may be used in immunohistochemistry (IHC) staining and thus have diagnostic application.

Monoclonal antibodies usable in IHC are highly valuable in clinic. In particular, in the cancer field mAb validated for IHC are used to diagnose a cancer as benign or malignant, determine the stage and grade of a tumor, and identify the cell type and origin of a metastasis to find the site of the primary tumor. IHC validated mAb are also widely used to predict therapeutic response notably in breast carcinoma.

In this context, mAb that can be used for both therapeutic and diagnostic (i.e., target detection) purposes are of crucial interest in clinic because they allow to determine patient eligibility to the treatment. Furthermore, the use of a unique and same antibody for diagnosis, prognosis and treatment is of considerable interest interm of reliability and cost development.

Thus, there remains a need to develop an anti-Nectin-4 being usable in diagnostic application though IHC assays, while having excellent therapeutic properties.

SUMMARY

The present disclosure relates to antibodies having specificity for Nectin-4 and uses thereof.

In particular, it is disclosed herein an anti-Nectin-4 antibody, which selectively binds to Nectin-4 in a biological sample in an IHC assay. More specifically, said antibody selectively binds to Nectin-4 in a tissue sample section, notably a fixed tissue sample and more particularly a Formaldehyde Fixed Paraffin Embedded (FFPE) tissue sample. Such antibody is thus usable for diagnosis and/or prognosis purposes.

In some embodiments, the anti-Nectin-4 antibody of the present disclosure binds Nectin-4, notably the human Nectin-4 of SEQ ID NO:1, with an apparent affinity-binding constant value ($K_D$) of less than 10 µg/mL, notably less 1 µg/mL, less than 100 ng/mL, less than 10 ng/mL or less than 5 ng/mL. Such antibody is thus typically usable for therapeutic application.

In specific embodiments, an anti-Nectin-4mAb according to the present disclosure competes for binding to Nectin-4 with the following reference murine antibody mAb 5A12.2 as obtainable by the hybridoma deposited at the CNCM under deposit number CNCM I-5407.

In specific embodiments, an anti-Nectin-4 antibody according to the present disclosure comprises a heavy chain and a light chain comprising the 6 CDRs of the antibody mAb 5A12.2, said mAb 5A12.2 being obtainable by the hybridoma deposited at the CNCM under deposit number CNCM I-5407. T Typically, the anti-Nectin-4 antibody of the present disclosure comprises:
- a HCDR1 of SEQ ID NO:2, a HCDR2 of SEQ ID NO:3, a HCDR3 of SEQ ID NO:4, a LCDR1 of SEQ ID NO:5, a LCDR2 of SEQ ID NO:6 and a LCDR3 of SEQ ID NO:7;
- a variable heavy chain (VH) domain and a variable light chain domain having at least 90% identity with the heavy chain and light chain of SEQ ID NO:8 and 9 respectively; and/or
- a variable heavy chain (VH) domain and a variable light chain of SEQ ID NO:8 and 9 respectively.

In specific embodiments, said anti-Nectin-4 antibody is a human, chimeric or humanized antibody.

In some embodiments of the present disclosure, the anti-Nectin-4 antibody is conjugated to a cytotoxic moiety.

Another aspect of the present disclosure relates to a nucleic acid molecule, which encodes a heavy chain and/or a light chain of any of the anti-Nectin-4 antibodies as described above.

The disclosure also pertains to a host cell comprising such nucleic acids, in particular for use in the manufacturing of any one of the anti-Nectin-4 antibodies as described above.

Another aspect of the disclosure relates to the anti-Nectin-4 antibodies as defined above, for use in therapy, notably for use in cancer treatment in particular for breast cancer, ovarian cancer or lung cancer treatment. Typically, the cancer is a metastatic cancer.

The disclosure also encompasses a composition comprising an anti-Nectin-4 antibody according to the present disclosure and at least a pharmaceutically acceptable carrier.

Another aspect of the disclosure relates to an in vitro method for diagnosing cancer in a subject comprising performing an IHC assay on a tissue sample from said subject using an anti-Nectin-4 antibody as herein disclosed, optionally wherein the tissue sample is a fixed tissue sample, notably a fixed embedded tissue sample from said subject, more particularly a Formaldehyde Fixed Paraffin Embedded (FFPE) tissue sample.

Another aspect of the disclosure relates to an in vitro method for determining the eligibility of a subject to a treatment with an anti-Nectin-4 antibody as herein described, comprising performing an IHC assay on a tissue sample section from said subject using said anti-Nectin-4 antibody, optionally wherein the tissue sample section is a fixed tissue, notably a fixed embedded tissue sample section from said subject, more particularly a Formaldehyde Fixed Paraffin Embedded (FFPE) tissue section.

The disclosure also relates to a method of treating cancer, in a subject in need thereof comprising administering to the subject, a therapeutically effective amount of the anti-Nectin-4 antibody as defined above. In a specific embodiment said method for treating cancer comprises a prior step of diagnosing cancer or of determining patient eligibility to a treatment with the anti-Nectin-4 antibody, comprising using said anti-Nectin-4 antibody in an IHC assay performed on a tissue sample section from said subject. In particular, the present disclosure encompasses a method of treatment of a patient suffering from or suspected of suffering from a cancer comprising:

- a step 1) of assessing Nectin-4 expression in a tissue sample from a subject suspected of having cancer, or of assessing responsiveness of said cancer patient to an anti-cancer therapeutic agent comprising:
  - (1a) contacting said tissue sample with the antibody or antigen binding fragment thereof as herein disclosed;
  - (1b) detecting the binding of said antibody or antigen binding fragment thereof to said tissue sample; and
  - (1c) determining the expression of Nectin-4 in the tissue sample, wherein the expression level of Nectin-4 in the tissue sample is compared with a reference expression level of Nectin-4; and
- a step 2) of administering said anti-cancer therapeutic agent to the patient when an increased expression level of Nectin-4 compared to the reference is observed;
- optionally wherein, the expression level of Nectin-4 is detected using an immunohistochemistry (IHC) approach, an immunoblotting assay, a fluorescence activated cell sorting (FACS) assay, or an Enzyme-Linked Immunosorbent Assay (ELISA),
- optionally wherein, the anti-cancer therapeutic agent comprises an anti-Nectin-4 antibody or an antibody drug conjugate of an anti-Nectin-4 antibody, typically of an antibody according to the present disclosure or a variant thereof.

DETAILED DESCRIPTION OF THE INVENTION

Definitions

As used herein, the term "Nectin-4" has its general meaning in the art and includes human Nectin-4, in particular the native-sequence polypeptide, isoforms, chimeric polypeptides, all homologs, fragments, and precursors of human Nectin-4. The amino acid sequence for native Nectin-4 includes the NCBI Reference Sequence: NP_112178.2.

More specifically the term "Nectin-4" includes the human Nectin-4 of the following SEQ ID:1

```
MPLSLGAEMWGPEAWLLLLLLLASFTGRCPAGELETSDVVTVVLGQDAK
LPCFYRGDSGEQVGQVAWARVDAGEGAQELALLHSKYGLHVSPAYEGRV
EQPPPPRNPLDGSVLLRNAVQADEGEYECRVSTFPAGSFQARLRLRVLV
PPLPSLNPGPALEEGQGLTLAASCTAEGSPAPSVTWDTEVKGTTSSRSF
KHSRSAAVTSEFHLVPSRSMNGQPLTCVVSHPGLLQDQRITHILHVSFL
AEASVRGLEDQNLWHIGREGAMLKCLSEGQPPPSYNWTRLDGPLPSGVR
VDGDTLGFPPLTTEHSGIYVCHVSNEFSSRDSQVTVDVLDPQEDSGKQV
DLVSASVVVVGVIAALLFCLLVVVVVLMSRYHRRKAQQMTQKYEEELTL
TRENSIRRLHSHHTDPRSQPEESVGLRAEGHPDSLKDNSSCSVMSEEPE
GRSYSTLTTVREIETQTELLSPGSGRAEEEEDQDEGIKQAMNHFVQENG
TLRAKPTGNGIYINGRGHLV
```

As used herein the term "antibody" or "immunoglobulin" have the same meaning, and will be used equally in the present disclosure.

The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments.

In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. According the variable regions of the light and heavy chains typically comprise 4 framework regions and 3 CDRs of the following sequence: FR1-CDR1-FR2-CDR2-FR3-CDR3-FR4. As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. According to the Kabat numbering system, the CDRs of the heavy chain variable domain are located at residues 31-35 (H-CDR1), residues 50-65 (H-CDR2) and residues 95-102 (H-CDR3) and the CDRs of the light chain variable domain are located at residues 24-34 (L-CDR1), residues 50-56 (L-CDR2) and residues 89-97 (L-CDR3). According to IMGT numbering for V (variable) domain, in the heavy chain, CDR1-IMGT region of comprises positions 26 to 33; the CDR2-IMGT region comprises positions 51 to 58; and the CDR3-IMGT region comprises position 97 to 109. In the light chain, CDR1-IMGT region of comprises positions 27 to 32; the CDR2-IMGT region comprises positions 50 to 52; and the CDR3-IMGT region comprises position 89 to 94.

In specific embodiments, an antibody provided herein is an antibody fragment, and more particularly any protein including an antigen-binding domain of an antibody as disclosed herein. Antibody fragments include, but are not limited to, Fv, Fab, F(ab')2, Fab', dsFv, scFv, sc(Fv)2 and diabodies.

An "isolated antibody", as used herein, refers to an antibody that is substantially free of other antibodies having different antigenic specificities (e.g., an isolated antibody that specifically binds to Nectin-4 is substantially free of antibodies that specifically bind to other antigens than Nectin-4). An isolated antibody that specifically binds to Nectin-4 may, however, have cross-reactivity to other antigens, such as related Nectin-4 molecules from other species. Moreover, an isolated antibody may be substantially free of other cellular material and/or chemicals.

Antibody affinity refers to the strength with which the antibody binds to the epitope presented on an antigen, such as a Nectin-4 in the present disclosure, through its antigen-binding site (paratope). The apparent affinity-binding constant value ($K_D$) for Nectin-4 may be assessed by flow cytometry by measuring the saturation curve of antibody binding and by determination of the EC50 value. This is illustrated in the examples performed on a cell-line expressing Nectin-4, such as a cancer cell line or a cell expressing recombinant Nectin-4 (see notably the Material and Methods section).

The term "$K_D$", as used herein, is intended to refer to the equilibrium dissociation constant, which is obtained from the ratio of Kd to Ka (i.e., Kd/Ka) and is expressed as a molar concentration (M). The $K_D$ value relates to the concentration of antibody (the amount of antibody needed for a particular experiment) and so the lower the $K_D$ value (lower concentration) and thus the higher the affinity of the antibody. The $K_D$ value for an antibody can also be determined using methods well established in the art. For example, methods for determining the $K_D$ values of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. A method for determining the $K_D$ of an antibody is by using surface plasmon resonance or using a biosensor system such as a Biacore® or Octet® systems. Kd is typically measured using surface plasmon resonance assays using a BIACORE®-2000 or a BIACORE®-3000 (BIAcore, Inc., Piscataway, NJ) at 25° C. with immobilized antigen CM5 chips at −10 response units (RU). Briefly, carboxymethylated dextran biosensor chips (CM5, BIACORE, Inc.) are activated with A/-ethyl-/V-(3-dimethylaminopropyl)-carbodiimide hydrochloride (EDC) and/V-hydroxysuccinimide (NHS) according to the supplier's instructions. Antigen is diluted with 10 mM sodium acetate, pH 4.8, to 5 pg/ml (−0.2 µM) before injection at a flow rate of 5 µl/minute to achieve approximately 1 0 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen et al. J. Mol. Biol. 293: 865-881, 1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "specificity" refers to the ability of an antibody to detectably bind an epitope presented on an antigen, such as Nectin-4. In the present disclosure, it is typically, while having relatively little detectable reactivity with non-Nectin-4 proteins or structures (such as other proteins presented on cancerous cell, or on other cell types), intended to refer to an antibody or protein that binds to human Nectin-4 expressed typically in a cancer cell line (such as SUM190 cancer cell line) as described in the examples, preferably with an apparent affinity-binding constant value ($K_D$) (or an EC50) of less than 10 µg/mL, notably less 1 µg/mL, less than 100 ng/mL, less than 10 ng/mL or less than 5 ng/mL as determined in the Examples and FIG. 2. Typically, apparent affinity-binding constant value ($K_D$) is not less than 0.05 ng/ml, notably 0.1 ng/ml. Generally, apparent affinity-binding constant value ($K_D$) (that can be determined as illustrated in the examples) is comprised between 0.1 ng and 10 µg/ml. In some embodiments, it binds to an antigen recombinant polypeptide with a $K_D$ of 10 nM or less, 1 nM or less, 100 pM or less, or 10 pM or less. Typically, the $K_D$ is not less than 0.05 pM notably 0.1 pM. Generally, the $K_D$ is comprised between 0.1 pM and 10 nM.

Figure 2:
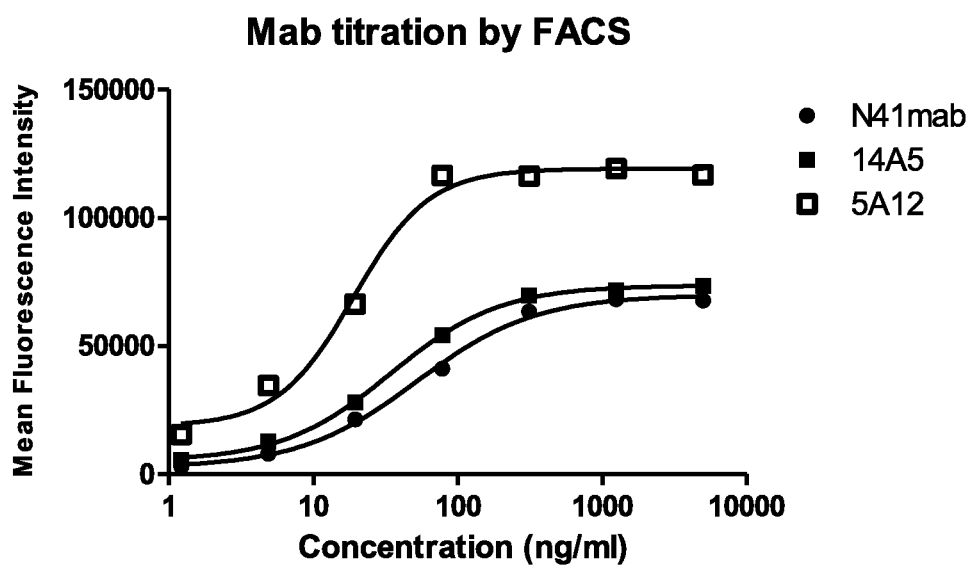

An antibody that "cross-competes for binding with Nectin-4" with the reference antibody mAb 5A12.2 is intended to refer to an antibody that binds Nectin-4 with an apparent affinity-binding constant value ($K_D$) (or an EC50) of less than 10 µg/mL, notably less 1 µg/mL, less than 100 ng/mL, less than 10 ng/mL or less than 5 ng/mL as determined in the Examples and FIG. 2. An antibody that "does not cross-compete with a particular antigen" is intended to refer to an antibody that binds to that antigen, with a $K_D$ of 100 nM or greater, or a $K_D$ of 1 µM or grater, or a $K_D$ of 10 µM or greater. In certain embodiments, such antibodies that do not cross-react with the antigen exhibit essentially undetectable binding against these proteins in standard binding assays.

The phrases "an antibody recognizing an antigen" and "an antibody having specificity for an antigen" are used interchangeably herein with the term "an antibody which binds specifically to an antigen".

"Selective binding" typically means that the antibody binds more strongly to a target, such as an epitope, for which it is specific as compared to the binding to another target. The antibody binds more strongly to a first target as compared to a second target if its affinity for the first target is higher than its affinity for the second target. Typically, an antibody binds more strongly to a first target as compared to a second target if it binds to the first target with a dissociation constant (Kd), or an EC50 as mentioned above, that is lower than the dissociation constant, or the EC50, for the second target. Most specifically the agent does not bind at all to the second target to a relevant extent, or has relatively little detectable reactivity (typically in an IHC assay it has no detectable staining, notably by qualitative visual inspection or by quantitative analysis, wherein the staining level is less than a reference value) with non-Nectin-4 proteins or structures (such as other proteins presented on cancerous cell, or on other cell types).

Selectivity can also be further exhibited by, e.g., an about 10:1, about 20:1, about 50:1, about 100:1, 10.000:1 or greater ratio of affinity in binding to the specific antigen versus non-specific binding to other irrelevant molecules (in this case the specific antigen is a Nectin-4 polypeptide).

Selective binding of an antibody in an IHC assay as herein disclosed may be further assessed as illustrated in the Example on a tissue sample (notably on a cancer tissue sample expressing Nectin-4). Typically, selective Nectin-4 binding of an antibody as herein disclosed in a tissue sample section in an IHC assay, can be assessed qualitatively by identifying the nature of Nectin-4 staining. When compared with a similar IHC assay performed on a control negative tissue sample (i.e., not expressing Nectin-4), an intercellular junctional staining is observed in a cancer/tumor tissue sample with an anti-nectin-4 antibody as herein disclosed. Indeed, as the protein is a transmembrane cell adhesion molecule, identifiable membranous staining is an indicator of a selective binding. In certain embodiments, selective anti-Nectin-4 antibodies of the present disclosure exhibit essentially undetectable staining of non Nectin-4 antigens. Thus, typically in such embodiment, a selective anti-Nectin-4 antibody only exhibits an intercellular junctional staining and has essentially undetectable intracellular staining.

Specificity can also be controlled by a competition assay, wherein the anti-Nectin-4 mAb is preincubated with recombinant soluble Nectin-4 IgV domain, prior IHC experiment. The lack of detectable staining is therefore indicative of the selectivity of the anti-Nectin-4 antibody as herein disclosed.

Staining can also be quantitatively analysed and thus results can be scored (QuickScore) by multiplying the percentage of positive cells (P) (maximum value is 100%) by the staining intensity (I) (Scale from 0 (no expression) to 3 (maximum expression as defined in (M-Rabet et al. "*Nectin-4: a new prognostic biomarker for efficient therapeutic targeting of primary and metastatic triple-negative breast cancer*". Ann Oncol. 2017 Apr. 1; 28(4):769-776)). Formula: QS=P×I. Maximum score is 300.A 'Nectin-4-high group' (QS>100) and a 'Nectin-4-low group' (QS<100) can be distinguished. The 'Nectin-4 high group' refers to the group potentially eligible for therapy with the 5A12.2 derived ADC. Thus, in one embodiment, an anti-Nectin 4 antibody as herein disclosed exhibits a QS score, as above described (see also Rabet et al., 2017 for reference with regards to the implementation of the assay), of at least 100.

The term "identity" refers to the sequence similarity between two polypeptide molecules or between two nucleic acid molecules. When a position in both compared sequences is occupied by the same base or same amino acid residue, then the respective molecules are identical at that position. The percentage of identity between two sequences corresponds to the number of matching positions shared by the two sequences divided by the number of positions compared and multiplied by 100. Generally, a comparison is made when two sequences are aligned to give maximum identity. The identity may be calculated by alignment using, for example, the GCG (Genetics Computer Group, Program Manual for the GCG Package, Version 7, Madison, Wisconsin) pileup program, or any of sequence comparison algorithms such as BLAST, FASTA or CLUSTALW.

A functional variant of the reference molecule according to the present disclosure exhibits functional properties that are substantially equal or superior to the corresponding functional properties of the reference molecule (e.g., the 5A12.2 mAb). By substantially equal it is herein intended that said functional variant retains at least about 50%, 60%, 70%, 80%, 90%, 95% or 100% of the corresponding functional property of the reference molecule.

In one aspect, the present disclosure relates to an anti-Nectin-4 antibody, wherein said antibody has at least one and more specifically both of the following properties:
(i) it binds Nectin-4, notably human Nectin-4 of SED ID NO: 1, with an apparent affinity-binding constant value ($K_D$) (or an EC50) of less than 10 µg/mL, notably less 1 µg/mL, less than 100 ng/mL, less than 10 ng/mL or less than 5 ng/mL;
(ii) it binds to Nectin-4 in an immunohistochemistry (IHC) assay. More specifically, said antibody selectively binds to Nectin-4 in a biological sample section in an IHC assay.

The anti-Nectin-4 antibodies of the present disclosure having such advantageous properties can be screened among anti-Nectin-4 antibodies using the IHC assay and/or affinity assay as described in the Examples.

In certain embodiments the cancer is carcinoma, lymphoma (including Hodgkin's and non-Hodgkin's lymphoma), blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, or various types of head and neck cancer. Typically, cancer as per the present disclosure includes local or metastatic breast, ovarian, bladder, urothelial, pancreatic and lung cancers or carcinomas.

Immunohistochemistry (IHC) is a routine laboratory technique used to visualize proteins in tissue or tissue sections using antibodies conjugated to enzymatic or fluorescent labels. Typically, said IHC assay is performed on a fixed tissue section. Fixation may be achieved using formaldehyde typically 4%), neutral buffer formalin (typically 10%). Most specifically, the tissue section is fixed and embedded. In a specific embodiment the IHC assay is a Formaldehyde Fixed Paraffin Embedded (FFPE) IHC assay. IHC techniques are further described in Immunohistochemical Staining Methods. Thomas Boenisch, ed. (3rd ed. 2001).

By "biological sample" is meant a collection of similar cells obtained from a subject or patient. A biological sample can be a tissue or a cell sample. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The biological sample can also be obtained from in vitro tissue or cell culture. The tissue sample may contain compounds which are not naturally intermixed with the tissue in nature such as preservatives, anticoagulants, buffers, fixatives, nutrients, antibiotics, or the like. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In specific embodiments the biological sample is a tissue sample, notably a fixed tissue sample, and more particularly paraffin-embedded tissue sample.

In some embodiments, the biological sample is from a subject having, predisposed to, or being tested for a cancer. More specifically also the tissue is a cancer tissue sample. By "cancer tissue", it is herein intended that the tissue is obtained from a subject suffering from a cancer and is taken from an organ or from a tissue affected by cancer. In other embodiments, the biological sample is from a subject having a cancer as above mentioned and in particular having a local or metastatic breast, ovarian, bladder, urothelial, pancreatic and luger lung cancers or carcinomas.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

The term "detection" includes any means of detecting, including direct and indirect detection. The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The terms "level of expression" or "expression level" in general are used interchangeably and generally refer to the amount of a polynucleotide, mRNA, or an amino acid product or protein in a biological sample. "Expression" generally refers to the process by which gene-encoded information is converted into the structures present and operating in the cell. Therefore, according to the disclosure "expression" of a gene (e.g., the Nectin-4 gene) may refer to transcription into a polynucleotide, translation into a protein, or even posttranslational modification of the protein.

Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. In some embodiments, "expression level" refers to amount of a protein (e.g., Nectin-4) in a biological sample as determined using methods known in the art or described herein, including but not limited to immunohistochemistry (IHC), immunoblotting (e.g., Western blotting), immunofluorescence (IF), flow cytometry, for example Fluorescence-Activated Cell Sorting (FACS™), or Enzyme-Linked Immunosorbant Assay (ELISA).

"Increased expression," "increased expression level," "increased levels," "elevated expression," "elevated expression levels," or "elevated levels" refers to an increased expression or increased levels of a biomarker in an individual relative to a control, such as an individual or individuals who are not suffering from the disease or disorder (e.g., cancer) or an internal control (e.g., a housekeeping biomarker).

"Decreased expression," "decreased expression level," "decreased levels," "reduced expression," "reduced expression levels," or "reduced levels" refers to a decrease expression or decreased levels of a biomarker in an individual relative to a control, such as an individual or individuals who are not suffering from the disease or disorder (e.g., cancer) or an internal control (e.g., a housekeeping biomarker). In some embodiments, reduced expression is little or no expression.

The term "primary antibody" as used herein refers to an antibody which binds specifically to the target protein antigen in a tissue sample. A primary antibody is generally the first antibody used in an immunohistochemical procedure. The primary antibody can be the only antibody used in an immunohistochemical procedure. The term "secondary antibody" as used herein refers to an antibody which binds specifically to a primary antibody, thereby forming a bridge between the primary antibody and a subsequent reagent, if any. The secondary antibody is generally the second antibody used in an immunohistochemical procedure.

Reference Antibody mAb 5A12.2

Antibodies as herein disclosed include the reference murine monoclonal antibody 5A12.2, as produced by the hybridoma, which has been deposited at Collection Nationale de Cultures des Microorganismes (CNCM, Institut Pasteur, 25 rue du Docteur Roux, 75724 Paris Cedex 15, France), in accordance with the terms of the Budapest treaty on Mar. 20, 2019, under the respective deposit number CNCM I-5407.

In particular embodiments, an anti-Nectin-4 antibody of the present disclosure, preferably a humanized anti-Nectin-4 antibody, comprises a heavy chain and a light chain comprising the 6 CDRs of the antibody mAb 5A12.2, said mAb 5A12.2 being obtainable by the hybridoma deposited at the CNCM under deposit number CNCM I-5407.

The present disclosure further relates to any antibodies, notably humanized antibodies, comprising the respective VH and VL regions of the above reference antibody.

The present disclosure further relates to said hybridoma accessible at the CNCM under deposit number CNCM I-5407.

The mAb 5A12.2 comprises:
a HCDR1 of SEQ ID NO:2, a HCDR2 of SEQ ID NO:3, a HCDR3 of SEQ ID NO:4, a LCDR1 of SEQ ID NO:5, a LCDR2 of SEQ ID NO:6 and a LCDR3 of SEQ ID NO:7; and
a variable heavy chain (VH) domain and a variable light chain domain having at least 90% identity with the heavy chain and light chain of SEQ ID NO:8 and 9 respectively.

The reference antibody mAb 5A12.2 binds the IgV-like distal domain (domain used to immunize mice) in the extracellular region of Nectin-4. Typically said reference antibody does not cross-compete with Ha22-2 mAb (Seattle Genetics) or any of the antibodies as disclosed in WO2017042210 and WO2018158398 (notably N41mAb and 14A5.2 mAb) for binding to Nectin-4, indicating that the present antibody binds to a distinct epitope. Cross-competion assay can be performed in indicated in the Example (see Material and Methods section).

Other antibodies as disclosed herein include those having amino acids that have been mutated by amino acid deletion, insertion or substitution, yet have at least 60, 70, 80, 90, 95, 96, 97, 98, 99 or percent identity in the CDR regions with the CDR regions of the reference mAb 5A12.2. Typically as per the present disclosure, antibodies may have between 1, 2, 3 or 4 amino acid variations (including deletion, insertion or substitution) in one or more CDRs, as compared to the CDR sequences of the reference antibody mAb 5A12.2.

In some embodiments, the antibody of the present disclosure is a mutant variant of the reference mAb 5A12.2, having the 6 CDR regions 100% identical to the corresponding 6 CDR regions of said reference mAb 5A12.2, and wherein said mutant variant antibody include mutant amino acid sequences wherein no more than 1, 2, 3, 4 or 5 amino acids have been mutated by amino acid deletion, insertion or substitution in the FR1, FR2, FR3 and FR4 regions when compared with the corresponding framework regions of the reference antibody.

Functional Variant Antibodies

In yet another embodiment, a functional variant antibody of the present disclosure has full length heavy and light chain amino acid sequences; or variable region heavy and light chain amino acid sequences, or all 6 CDR regions amino acid sequences that are homologous or more specifically identical to the corresponding amino acid sequences of the antibody mAb 5A12.2 described above (as set forth in SEQ ID NO:2 to 7), and wherein such functional variant antibodies retain the desired functional properties of the original mAb 5A12.2 antibody.

A functional variant of the reference mAb 5A12.2 antibody, notably a functional variant of a VL, VH, or CDR used in the context of a monoclonal antibody of the present disclosure still allows the antibody to retain at least a substantial proportion (at least about 50%, 60%, 70%, 80%, 90%, 95% or 100%) of the affinity (typically assessed by $K_D$ or binding EC50 as measured by flow cytometry for example on a cell-line expressing Nectin-4 such as a cancer cell line), and/or the selectivity of the parent antibody (e.g.: mAb 5A12.2) and in some cases such a monoclonal antibody of the present disclosure may be associated with greater affinity, selectivity and/or specificity than the parent Ab (e.g.: mAb 5A12.2).

In some embodiments, an anti-Nectin 4 antibody which is a functional variant of the reference mAb 5A12.2 antibody as herein disclosed has a variable heavy chain (VH) domain and a variable light chain domain having at least 90% identity with the amino acid sequences SEQ ID NO:8 and 9 respectively.

Desired functional properties of the original mAb 5A12.2 antibody may be selected from the group consisting of:
i. it binds Nectin-4, notably to human Nectin-4 of SEQ ID NO: 1, with an apparent affinity-binding constant value ($K_D$) (or an EC50) of less than 10 µg/mL, notably less 1 µg/mL, less than 100 ng/mL, less than 10 ng/mL or less than 5 ng/mL (typically comprised between 0.05 ng and 10 µg/ml, notably between 0.1 ng and 1 µg/ml);
ii. it binds to Nectin-4 in an immunohistochemistry (IHC) assay. More specifically, said antibody selectively binds to Nectin-4 in a biological sample section in an IHC assay For example, the present disclosure relates to functional variant antibodies of the reference mAb 5A12.2, comprising a variable heavy chain (VH) and a variable light chain ($V_L$) sequences where the CDR sequences, i.e. the 6 CDR regions; HCDR1, HCDR2, HCDR3, LCDR1, LCDR2, LCDR3 share at least 60, 70, 90, 95 or 100 percent of sequence identity to the corresponding CDR sequences of the reference mAb 5A12.2 (as respectively defined in SEQD ID NO:2-7), wherein said functional variant antibody specifically binds to Nectin-4, and the antibody exhibits at least one of the following functional properties:
  (i) it binds Nectin-4 with an apparent affinity-binding constant value ($K_D$) (or an EC50) of less than 10 μg/mL, notably less 1 μg/mL, less than 100 ng/mL, less than 10 ng/mL or less than 5 ng/mL (typically comprised between 0.05 ng and 10 μg/ml, notably between 0.1 ng and 1 μg/ml);
  (ii) it binds to Nectin-4 in an immunohistochemistry (IHC) assay. More specifically, said antibody selectively binds to Nectin-4 in a biological sample section in an IHC assay.

It further relates to functional variant antibodies of the mAb 5A12.2 reference antibody comprising a heavy chain variable region and a light chain variable region that are at least 80%, 90%, or at least 95, 96%, 97%, 98%, 99% or 100% identical the corresponding heavy and light chain variable regions of said mAb 5A12.2 reference antibody (as set forth respectively in SEQ ID NO 8 and 9); the functional variant antibody specifically binds to Nectin-4, and exhibits at least one of the following functional properties:
  (i) it binds Nectin-4 with an apparent affinity-binding constant value ($K_D$) (or an EC50) of less than 10 μg/mL, notably less 1 μg/mL, less than 100 ng/mL, less than 10 ng/mL or less than 5 ng/mL (typically comprised between 0.05 ng and 10 μg/ml, notably between 0.1 ng and 1 μg/ml);
  (ii) it binds to Nectin-4 in an immunohistochemistry (IHC) assay. More specifically, said antibody selectively binds to Nectin-4 in a biological sample section in an IHC assay.

In various embodiments, the antibody may exhibit one or two of the desired functional properties discussed above. The antibody can be, for example, a human antibody, a humanized antibody or a chimeric antibody. Preferably the antibody or protein is a humanized human antibody, more preferably a humanized silent antibody.

As used herein, the term "silent" antibody refers to an antibody that exhibits no or low ADCC activity as measured in an in vitro ADCC activity assay measuring cell lysis of target cells.

In one embodiment, the term "no or low ADCC activity" means that the silent antibody exhibits an ADCC activity that is at below 50%, for example below 10% of the ADCC activity that is observed with the corresponding wild type (non silent) antibody for example with a wild type human IgG1 antibody. Preferably, no detectable ADCC activity is observed in an in vitro ADCC activity assay with a silent antibody as compared to a control Fab antibody.

Silenced effector functions can be obtained by mutation in the Fc constant part of the antibodies and have been described in the Art: Strohl 2009 (LALA & N297A); Baudino 2008, D265A (Baudino et al., J. Immunol. 181 (2008): 6664-69, Strohl, CO Biotechnology 20 (2009): 685-91). Examples of silent IgG1 antibodies comprise mutations reducing ADCC at positions 234, 235 and/or 331 in the IgG1 Fc amino acid sequence (EU numbering). Another silent IgG1 antibody comprises the N297A mutation, which results in aglycosylated or non-glycosylated antibodies.

The sequences of the CDR variants may differ from the sequence of the CDRs of the parent antibody sequences through mostly conservative substitutions; for instance, all or 10 or more, such as 9, 8, 7, 6, 5, 4, 3, 2 or 1 or more of the substitutions in the variant are conservative amino acid residue replacements. In the context of the present disclosure, conservative substitutions may be defined by substitutions within the classes of amino acids reflected as follows:
  Aliphatic residues I, L, V, and M
  Cycloalkenyl-associated residues F, H, W, and Y
  Hydrophobic residues A, C, F, G, H, I, L, M, R, T, V, W, and Y
  Negatively charged residues D and E
  Polar residues C, D, E, H, K, N, Q, R, S, and T
  Positively charged residues H, K, and R
  Small residues A, C, D, G, N, P, S, T, and V
  Very small residues A, G, and S
  Residues involved in turn A, C, D, E, G, H, K, N, Q, R, S, P, and formation T
  Flexible residues Q, T, K, S, G, P, D, E, and R More conservative substitutions groupings include valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of the present reference antibody. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide. According to the present disclosure, a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present disclosure a first amino acid sequence having at least 50% of identity with a second amino acid sequence means that the first sequence has 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the antibody of the present disclosure is a chimeric antibody, typically a chimeric mouse/human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the VH and the VL domains of the present reference antibody.

In some embodiments, the antibody of the present disclosure is a humanized antibody. In specific embodiments, the antibody of the present disclosure is a humanized antibody which comprises the 6 CDRs of the present reference antibody. As used herein the term "humanized antibody" refers to antibodies in which the framework regions (FRs) have been modified to comprise the FRs from a donor immunoglobulin of different species (for example human species) as compared to that of the parent immunoglobulin (for example murine CDRs).

In some embodiments, the antibody of the present disclosure is selected from the group consisting of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH:VL heterodimer which is usually expressed from a gene fusion including VH and VL encoding genes linked by a peptide-encoding linker. The human scFv fragment of the disclosure includes CDRs that are held in appropriate conformation, preferably by using gene recombination techniques.

Functional variant antibodies with mutant amino acid sequences can be obtained by mutagenesis (e.g., site-directed or PCR-mediated mutagenesis) of the coding nucleic acid molecules, followed by testing of the encoded altered antibody for retained function (i. e., the functions set forth above) using the functional assays described herein.

Antibodies that Cross-Compete the Reference mAb 5A12.2

Additional antibodies with similar advantageous properties of the reference antibody mAb 5A12.2 as disclosed herein can be identified based on their ability to cross-compete with (e.g., to competitively inhibit the binding of), in a statistically significant manner with said reference antibody mAb 5A12.2 as described above, in standard Nectin-4 competition binding assays (see ref. 7).

In some embodiment, the test antibody may first be screened for their binding affinity to Nectin-4, for example from human recombinant antibody libraries using for example phage display technologies or from transgenic mouse expressing human variable region antibodies immunized with Nectin-4 antigens.

The ability of a test antibody to cross-compete with or inhibit the binding of antibodies of the present disclosure to human Nectin-4 demonstrates that the test antibody can compete with that antibody for binding to human Nectin-4; such an antibody may, according to non-limiting theory, bind to the same or a related (e.g., a structurally similar or spatially proximal) epitope on human Nectin-4 as the antibody with which it competes. As used herein, an antibody "competes" for binding when the competing antibody inhibits Nectin-4 binding of an antibody or antigen binding fragment of the present disclosure by more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% in the presence of an equimolar concentration of competing antibody.

In some embodiments the antibodies or antigen binding fragments of the present disclosure bind to one or more epitopes of Nectin-4. In some embodiments, the epitopes to which the present antibodies or antigen binding fragments bind are linear epitopes. Typically, however, the epitopes to which the present antibodies or antigen binding fragments bind are non-linear, conformational epitopes.

In some embodiments an antibody according to the present disclosure binds to a distinct epitope as to Ha22-2 mAb (Seattle Genetics) or any of the antibodies as disclosed in WO2017042210 and WO2018158398 (notably N41 mAb and 14A5.2 mAb). Typically, an antibody as herein disclosed does not cross-compete with Ha22-2 mAb (Seattle Genetics) or any of the antibodies as disclosed in WO2017042210 and WO2018158398 (notably N41 mAb and 14A5.2 mAb) for binding to Nectin-4. Cross-competition assay can be performed in indicated in the Example (see Material and Methods section).

In one embodiment, the present disclosure provides antibodies that bind to the same epitope as do the presently disclosed reference antibody (i.e.: mAb 5A12.2).

The antibodies of the present disclosure may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al, eds, 1994 Current Protocols in Molecular Biology, Vol. 1, John Wiley & sons, Inc., New York).

For example, to screen an anti-Nectin-4 antibody for its ability to binds to the same epitope or to compete with the reference antibody mAb 5A12.2 for binding cells (such as cancer cell lines expressing Nectin-4) can be stained with saturing concentration of said reference antibody. After washing, different doses of test anti-Nectin-4 mAb scan be tested for their competitive potential with the reference antibody. The mAbs that do compete for the same binding site as the reference antibody will not be able to recognize Nectin-4 in the presence of such reference antibody. The data can be expressed as mean fluorescence intensity.

The antibodies of the present disclosure are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, antibodies of the present disclosure can be synthesized by recombinant DNA techniques well-known in the art.

For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In one embodiment, the present disclosure provides an isolated antibody which cross-blocks or is cross-blocked by the reference mAb 5A12.2, from binding to Nectin-4, wherein said antibody:
  (i) binds Nectin-4 with an apparent affinity-binding constant value ($K_D$) (or an EC50) of less than 10 µg/mL, notably less 1 µg/mL, less than 100 ng/mL, less than 10 ng/mL or less than 5 ng/mL;
  (ii) binds to Nectin-4 in an immunohistochemistry (IHC) assay. More specifically, said antibody selectively binds to Nectin-4 in a biological sample section in an IHC assay.

In specific embodiments, the disclosure provides antibodies that bind to the same epitope as do the reference mAb 5A12.2 as described herein.

In specific embodiments, the disclosure provides antibodies that do not compete for binding to Nectin-4 with Ha22-2 mAb (Seattle Genetics) or any of the antibodies as disclosed in WO2017042210 and WO2018158398 (notably N41mAb and 14A5.2 mAb).

Typically, an antibody that competes for binding to Nectin-4 with the reference mAb 5A12.2 according to the present disclosure still retains at least a substantial proportion (at least about 50%, 60%, 70%, 80%, 90%, 95% or 100%) of the affinity and/or the selectivity of the reference antibody (e.g.: mAb 5A12.2) and in some cases may be associated with greater affinity, selectivity and/or specificity than the reference antibody (e.g.: mAb 5A12.2).

In a certain embodiment, the cross-blocking antibody, that competes for binding to Nectin-4 with the reference mAb 5A12.2, is a chimeric, humanized or human recombinant antibody.

Generation of Transfectomas Producing Monoclonal Antibodies

The antibodies of the present disclosure are produced by any techniques known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, antibodies of the present disclosure can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the present disclosure relates to a nucleic acid molecule encoding an antibody according to the present disclosure as set forth in table 1. More particularly the nucleic acid molecule encodes a heavy chain or a light chain of an antibody of the present disclosure. More particularly the nucleic acid molecule comprises a VH or VL coding region having at least 70%, 80%, 90%, 95% or 100% of identity to the corresponding nucleic acid encoding heavy chain variable region (VH region) or light chain variable region (VL) of the reference antibody 5A12.2.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. So, a further object of the disclosure relates to a vector comprising a nucleic acid of the disclosure. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. Any expression vector for animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present disclosure relates to a host cell which has been transfected, infected or transformed by a nucleic acid and/or a vector as described above. As used herein, the term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids as herein disclosed may be used to produce an antibody of the present disclosure in a suitable expression system. The term "expression system" means a host cell and compatible vector under suitable conditions, e.g., for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolatereductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present disclosure also relates to a method of producing a recombinant host cell expressing an antibody according to the disclosure, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present disclosure.

Antibodies of the present disclosure are suitably separated from the culture medium by conventional immunoglobulin purification procedures such as, for example, protein A-Sepharose, hydroxylapatite chromatography, gel electrophoresis, dialysis, or affinity chromatography.

In some embodiments, the human chimeric antibody of the present disclosure can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody as herein disclosed may be produced by obtaining nucleic acid sequences encoding CDR domains, as previously described, constructing a humanized antibody expression vector by inserting them into an expression vector having genes encoding (i) a heavy chain constant region and heavy chain variable framework regions identical to that of a human antibody and (ii) a light chain constant region and light chain variable framework regions identical to that of a human antibody, and expressing the genes by introducing the expression vector into suitable cell line. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into cell lines, and balance between the expression levels of antibody H and L chains in cell lines, humanized antibody expression vector of the tandem type is preferred. Examples of tandem type humanized antibody expression vector include pKANTEX93 (WO 97/10354), pEE18 and the like.

Methods for humanizing antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present disclosure can be obtained by treating an antibody which specifically reacts with AMH with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present disclosure can be obtained treating an antibody which specifically reacts with AMH with a protease, pepsin. Also, the F(ab')2 can be produced by binding Fab' described below via a thioether bond or a disulfide bond.

The Fab' of the present disclosure can be obtained treating F(ab')2 which specifically reacts with AMH with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present disclosure can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv.

To generate a humanized scFv fragment, the well-known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

Engineered antibodies of the present disclosure further include those in which modifications have been made to framework residues within VH and/or VL, e.g., to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the disclosure. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

Fc Engineering

The antibody as herein disclosed can be characterized by one or more of the functional or structural features of the aspects described above, or by any combination of selected functional and structural features.

The antibody as herein disclosed may be of any isotype. The choice of isotype typically will be guided by the desired effector functions, such as ADCC silencing. Exemplary isotypes are IgG1, IgG2, IgG3, and IgG4. Either of the human light chain constant regions, kappa or lambda, may be used. If desired, the class of an antibody of the present disclosure may be switched by known methods. Typical, class switching techniques may be used to convert one IgG subclass to another, for instance from IgG1 to IgG2. Thus, the effector function of the antibodies of the present disclosure may be changed by isotype switching to, e.g., an IgG1, IgG2, IgG3, IgG4, IgD, IgA, IgE, or IgM antibody for various therapeutic uses. In some embodiments, the antibody as herein disclosed is a full-length antibody. In some embodiments, the full-length antibody is an IgG1 antibody. In some embodiments, the full-length antibody is an IgG4 antibody. In some embodiments, the Nectin-4-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antibodies are disclosed in WO2008145142.

In some embodiments, the antibody of the present disclosure does not comprise a Fc portion that induces antibody dependent cellular cytotoxicity (ADCC). The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, MD). In some embodiments, the antibody of the present disclosure does not comprise an Fc domain capable of substantially binding to a FcgRIIIA (CD16) polypeptide. In some embodiments, the antibody of the present disclosure lacks an Fc domain (e.g. lacks a CH2 and/or CH3 domain) or comprises an Fc domain of IgG2 or IgG4 isotype. In some embodiments, the antibody of the present disclosure consists of or comprises a Fab, Fab', Fab'-SH, F (ab') 2, Fv, a diabody, single-chain antibody fragment, or a multispecific antibody comprising multiple different antibody fragments. In some embodiments, the antibody of the present disclosure is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. Nos. 6,194,551.

Another modification of the antibodies herein that is contemplated by the present disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI—CIO) alkoxy- or aryloxy-poly-ethylene glycol or polyethylene glycol-maleimide. In some embodiments, the antibody to be pegylated is an aglycosylated antibody. Methods for pegylating proteins are known in the art and can be applied to the antibodies of the present disclosure. See for example, EP 0154 316 by Nishimura et al. and EP 0 401 384 by Ishikawa et al.

Another modification of the antibodies that is herein contemplated is a conjugate or a protein fusion of at least the antigen-binding region of the antibody of the present disclosure to serum protein, such as human serum albumin or a fragment thereof to increase half-life of the resulting molecule.

In some embodiments, the disclosure also provides a multispecific antibody. Exemplary formats for the multispecific antibody molecules of the disclosure include, but are not limited to (i) two antibodies cross-linked by chemical heteroconjugation, one with a specificity to Nectin-4 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., *Generation and Characterization of a Dual Variable Domain Immunoglobulin (DVD-Ig™) Molecule*, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies. In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present disclosure are prepared by a method comprising the following steps, wherein at least one of the first and second antibodies is the antibody of the present disclosure. a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present disclosure and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such asymmetrical mutations, optionally wherein one or both Fc-regions are of the IgG1 isotype.

Antibody-Drug Conjugates

In some embodiments, the antibody of the present disclosure is conjugated to a therapeutic moiety, i.e., a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxyanthracindione; a tubulin-inhibitor such as maytansine or an analog or derivative thereof, an antimitotic agent such as mo no methyl auristatin E or F or an analog or derivative thereof, dolastatin 10 or 15 or an analogue thereof, irinotecan or an analogue thereof, mitoxantrone; mithramycin; actinomycin D; 1-dehydrotestosterone; a glucocorticoid; procaine; tetracaine; lidocaine; propranolol; puromycin; calicheamicin or an analog or derivative thereof, an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof, an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, Aleuritesfordii proteins, dianthin proteins, Phytolaccaamericana proteins such as PAPI, PAPII, and PAP-S, momordicacharantia inhibitor, curcin, crotin, *Sapaonaria officinalis* inhibitor, gelonin, mitogellin, restrictocin, phenomycin, and enomycin toxins; ribonuclease (R ase); DNase I, Staphylococcal enterotoxin A; pokeweed antiviral protein; diphtherin toxin; and *Pseudomonas* endotoxin.

In some embodiments, the antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al, (1998) Antimicrob. Agents and Chemother. 42: 2961-2965). For example, auristatin E can be reacted with para-acetyl benzoic acid or benzoylvaleric acid to produce AEB and AEVB, respectively. Other typical auristatin derivatives include AFP, MMAF (monomethylauristatin F), and MMAE (monomethylauristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody is conjugated to Mertansine (also called emtansine or DM1) or a peptide analog, derivative or prodrug thereof. Mertansine is a tubulin inhibitor, meaning that it inhibits the assembly of microtubules by binding to tubulin.

In some embodiments, the antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al, Cancer Res 2010; 70(17): 6849-6858; Antonow D. et al, Cancer J 2008; 14(3): 154-169; Howard P. W. et al, Bioorg Med ChemLett 2009; 19: 6463-6466 and Sagnou et al, Bioorg Med ChemLett 2000; 10(18): 2083-2086.

In some embodiments, the antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethylauristatin E, monomethylauristatin F, a PDB, or an analog, derivative, or prodrug of any thereof.

In some embodiments, the antibody is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethylauristatin E or an analog, derivative or prodrug thereof. In some embodiments, the antibody is conjugated to monomethylauristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

In some embodiments, the antibody is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immuno stimulatory nucleic acid (e.g., an immunostimulatoryCpG motif-containing DNA molecule). In some embodiments, the antibody is conjugated to an aptamer or a ribozyme.

In some embodiments, the antibody is conjugated, e.g., as a fusion protein, to a lytic peptide such as CLIP, Magainin 2, mellitin, Cecropin and PI 8.

In some embodiments, the antibody is conjugated to a cytokine, such as, e.g., IL-2, IL-4, IL-6, IL-7, IL-10, IL-12, IL-13, IL-15, IL-18, L-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules Non-limiting examples of radioisotopes include $^3$H, $^{14}$C N $^{35}$S, $^{90}$Y "Tc, $^{125}$I, $^{131}$I, $^{186}$Re, $^{213}$Bi, $^{223}$Ac and $^{227}$Th. For therapeutic purposes, a radioisotope emitting beta- or alpha-particle radiation can be used, e.g., 1311, 90Y, 211At, 212Bi, 67Cu, 186Re, 188Re, and 212Pb.

Techniques for conjugating molecule to antibodies, are well-known in the art (See, e.g., Amon et al, "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy." in Monoclonal Antibodies For Cancer Detection And Therapy (Baldwin et al. eds., Academic Press, 1985); and Thorpe et al, 1982, Immunol. Rev. 62: 119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Haider, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target human epidermal growth factor receptor 2-positive breast cancer. Clin. Cancer Res. 16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

Pharmaceutical Compositions

In another aspect, the present disclosure provides a composition, e.g., a pharmaceutical composition, containing at least one antibody as disclosed herein, formulated together with a pharmaceutically acceptable carrier. Such compositions may include one or a combination of (e.g., two or more different) antibodies as described above. Pharmaceutical compositions disclosed herein also can be administered in combination therapy, i.e., combined with other agents.

For example, an antibody of the present disclosure may typically be combined with at least one antiviral, anti-inflammatory or another antiproliferative agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route.

Depending on the route of administration, the active compound, i.e., the antibody, may be coated in a material to protect the compound from the action of acids and other natural conditions that may inactivate the compound. The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Chimeric Antigen Receptors (CARs)

The present disclosure also provides chimeric antigen receptors (CARs) comprising an antigen binding domain of the antibody of the present disclosure. Typically, said chimeric antigen receptor comprises at least one VH and/or VL sequence of the antibody of the present disclosure. The chimeric antigen receptor the present disclosure also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

In some embodiments, the present disclosure provides CARs comprising an antigen-binding domain comprising, consisting of, or consisting essentially of, a single chain variable fragment (scFv) of the N41 mab antibody. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, and CD3ζ (intracellular domains. CD28 is a T cell marker important in T cell co-stimulation. 4-IBB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present disclosure can be glycosylated, amidated, carboxylated, phosphorylated, esterified, N-acylated, cyclized via, e.g., a disulfide bridge, or converted into an acid addition salt and/or optionally dimerized or polymerized.

The disclosure also provides a nucleic acid encoding for a chimeric antigen receptor of the present disclosure. In some embodiments, the nucleic acid is incorporated in a vector as such as described above.

The present disclosure also provides a host cell comprising a nucleic acid encoding for a chimeric antigen receptor of the present disclosure. While the host cell can be of any cell type, can originate from any type of tissue, and can be of any developmental stage, the host cell is a T cell, e.g., isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

The population of those T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are auto lymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologies and drugs to activate the immune function of the cells. Once the autologous cells are activated, these ex vivo activated cells are reinfused into the patient to enhance the immune system to treat cancer. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95° %) of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

In particular the cells of the present disclosure are particularly suitable for the treatment of cancer. According, a further object of the present disclosure relates to a method of treating cancer in a subject in need thereof comprising administering to the subject a therapeutically effective amount of a population of cells as herein disclosed.

Uses and Methods of the Invention

The antibodies or proteins of the present disclosure have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The methods are particularly suitable for treating, preventing or diagnosing Nectin-4-related disorders and in particular for treating, preventing or diagnosing cancers.

The disclosure also pertains to the methods of manufacturing a medicament for use in the prevention or treatment of cancer, said medicament comprising an anti-Nectin-4 antibody or a CAR as described in the previous sections.

As used herein, a "nectin-4-related disorder" includes conditions associated with or characterized by aberrant nectin-4 expression levels and/or diseases. In some embodiments, a "nectin-4-related disorder" includes conditions involving cells expressing Nectin-4.

In some embodiments, the present disclosure provides a method for killing a Nectin-4-expressing cell by contacting the cell with the antibody of the present disclosure. In some embodiments, the present disclosure provides a method for killing a Nectin-4-expressing cell by contacting the cell with the antibody of the present disclosure in the presence of effector cells capable of inducing an Fc-mediated effector cell response such as a CDC, ADCC or ADCP response. In this embodiment, the antibody is typically full-length and of an isotype leading to a CDC or ADCC response, such as, e.g., an IgG1 isotype. In some embodiments, the present disclosure provides a method for killing a Nectin-4-expressing cell by contacting the cell with an ADC of the present disclosure.

In some embodiments, the antibody of the present disclosure is particularly suitable for the treatment of cancer. Cancer cells over-expressing Nectin-4 are indeed good targets for the antibodies of the present disclosure, since more antibodies may be bound per cell. Thus, in one aspect, the disorder involving cells expressing Nectin-4 is cancer, i.e., a tumorigenic disorder, such as a disorder characterized by the presence of tumor cells expressing Nectin-4 including, for example, disorders where the cells are from a solid tumor or hematological tumor. In particular, the antibody of the present disclosure may be used as treatment of hyperproliferative diseases associated with Nectin-4 expression, overexpression or activation. In particular, the antibody of the present disclosure is particularly suitable for the treatment of breast cancer, ovarian cancer, bladder, pancreatic and lung cancer or carcinomas. As used herein, the term "breast cancer" as used herein includes, but is not limited to, all types of breast cancers at all stages of progression like metastatic breast cancer or breast carcinomas. In particular, the breast cancer is selected among triple-negative breast cancers (TNBC) that are distinguished by negative immunohistochemical staining for estrogen and progesterone receptors and human epidermal growth factor receptor-2 (HER2), and represent 15% of all breast cancers. The term "ovarian cancer" as used herein includes, but is not limited to, all types of ovarian cancers at all stages of progression like metastatic ovarian cancer or ovarian carcinomas. The term "lung cancer", as used herein, includes, but is not limited to, all types of lung cancers at all stages of progression like lung carcinomas metastatic lung cancer, non-small cell lung carcinomas or Small cell lung carcinoma.

In some embodiments, the antibody of the present disclosure is particularly suitable for the treatment of a metastatic cancer.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria (e.g., disease manifestation, etc.).

As used herein, the term "therapeutically effective amount" refers to an amount effective, at dosages and for periods of time necessary, to achieve a desired therapeutic result. A therapeutically effective amount of the antibody of the present disclosure may vary according to factors such as the disease state, age, sex, and weight of the individual, and the ability of the antibody of the present disclosure to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present disclosure depend on the disease or condition to be treated and may be determined by the persons skilled in the art. A physician having ordinary skill in the art may readily determine and prescribe the effective amount of the pharmaceutical composition required. For example, the physician could start doses of the antibody of the present disclosure employed in the pharmaceutical composition at levels lower than that required in order to achieve the desired therapeutic effect and gradually increase the dosage until the desired effect is achieved. In general, a suitable dose of a composition of the present disclosure will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to treat autoimmune disorders, for example, be evaluated in an animal model system predictive of efficacy in treating autoimmune disorders. Alternatively, this property of a composition may be evaluated by examining the ability of the compound to inhibit induction of immune response by in vitro assays known to the skilled practitioner. A therapeutically effective amount of a therapeutic compound may decrease immune or inflammatory response, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present disclosure is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present disclosure is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered overtime or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using a labeled antibody of the present disclosure, fragment or mini-antibody derived from the antibody of the present disclosure. If desired, an effective daily dose of a pharmaceutical composition may be administered as two, three, four, five, six or more sub-doses administered separately at appropriate intervals throughout the day, optionally, in unit dosage forms. In some embodiments, the human monoclonal antibodies of the present disclosure are administered by slow continuous infusion over a long period, such as more than 24 hours, in order to minimize any unwanted side effects. An effective dose of an antibody of the present disclosure may also be administered using a weekly, biweekly or triweekly dosing period. The dosing period may be restricted to, e.g., 8 weeks, 12 weeks or until clinical progression has been established. As non-limiting examples, treatment according to the present disclosure may be provided as a daily dosage of an antibody of the present disclosure in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

The present disclosure also provides for therapeutic applications where the antibody of the present disclosure is used in combination with at least one further therapeutic agent relevant for the disease or disorder to be treated, as described above. Such administration may be simultaneous, separate or sequential. For simultaneous administration, the agents may be administered as one composition or as separate compositions, as appropriate. The further therapeutic agent is typically relevant for the disorder to be treated. Exemplary therapeutic agents include other anti-cancer antibodies or ADCs, cytotoxic agents, immunotherapy, chemotherapeutic agents, anti-angiogenic agents, anti-cancer immunogens, cell cycle control/apoptosis regulating agents, hormonal regulating agents, and other agents described below.

Typically, the antibody of the present disclosure is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present disclosure may be administered orally, parenterally, by inhalation spray, topically, rectally, nasally, buccally, vaginally or via an implanted reservoir. The used herein includes subcutaneous, intravenous, intramuscular, intraarticular, intra-synovial, intrasternal, intrathecal, intrahepatic, intralesional and intracranial injection or infusion techniques. Sterile injectable forms of the compositions of this disclosure may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring, or coloring agents may also be added. Alternatively, the compositions of the present disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols. The compositions of the present disclosure may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of the present disclosure include, but are not limited to, mineral oil, liquid petrolatum, white petrolatum, propylene glycol, polyoxyethylene, polyoxypropylene compound, emulsifying wax, and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be carried out using a rectal suppository formulation (see above) or a suitable enema formulation. Patches may also be used. The compositions of the present disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

For example, an antibody present in a pharmaceutical composition of the present disclosure can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of the present disclosure may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the disclosure for injection (e.g., intramusculafr, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of an anti-Nectin-4 antibody of the present disclosure.

Diagnostic and Prognostic Methods

In one embodiment the present disclosure relates to a method of detecting the presence or the expression level of Nectin-4 in a biological sample from a subject, wherein the method comprises: contacting the biological sample with an anti-Nectin-4 antibody as herein disclosed and detecting the presence of the bound antibody.

Typically, the detection is performed by immunohistochemistry.

The biological sample is typically as previously described, notably the biological sample is a fixed tissue and more specifically an FFPE tissue.

The subject is typically as previously described The term "detecting" as used herein encompasses quantitative or qualitative detection. The present disclosure therefore comprises detecting the presence and/or expression level of Nectin-4 in the sample. Selective binding of the antibody to Nectin-4 is notably established by the presence of a membrane staining, as nectin-4 is a membrane protein.

In certain embodiments, the anti-Nectin-4 antibodies provided herein are useful for detecting the presence of Nectin-4 in a biological sample.

In one embodiment, an Nectin-4 antibody as herein disclosed for use in a method of diagnosis or detection is provided. In another instance, the disclosure provides for the use of an anti-Nectin-4 antibody as previously described in the manufacture of a reagent for use in a method of diagnosis or detection.

In one embodiment, for example, a method of detecting the presence of Nectin-4 in a biological sample, described below, is provided. In certain embodiments, the method comprises contacting the biological sample with an Nectin-4 antibody as described herein under conditions permissive for binding of the anti-Nectin-4 antibody to Nectin-4, and detecting whether a complex is formed between the anti-Nectin-4 antibody and Nectin-4. Such method may be an in vitro or in vivo method. Anti-Nectin-4 antibodies of the disclosure can be used, for example, in immunoassays, including, for example, immunohistochemistry (IHC), immunofluorescence (IF), immunoblotting (e.g., Western blotting), flow cytometry (e.g., FACS™), and Enzyme-linked Immunosorbant Assay (ELTSA). More specifically the immuno assay is IHC and the biological sample is a fixed tissue, notably FFPE.

In one embodiment, an anti-Nectin-4 antibody is used to select subjects eligible for therapy with an anti-Nectin-4 antibody (in particular with the same anti-Nectin-4 antibody), typically, where Nectin-4 is a biomarker for selection of patients. The disclosure further provides for the use of an anti-Nectin-4 antibody in a method of diagnosing a subject suffering from a disorder (e.g., a cancer), the method comprising: determining the presence or expression level of Nectin-4 in a sample obtained from the subject by contacting the sample with an anti-Nectin-4 antibody as previously herein described and detecting the presence of the bound antibody.

For example, the method provides for the use of an anti-Nectin-4 antibody in a method of diagnosing a subject suffering from a cancer, the method comprising: determining the presence or expression level of Nectin-4 in a sample obtained from the subject by contacting the sample with an anti-Nectin-4 antibody as previously herein described and detecting the presence of the bound antibody. In some embodiments, the sample is selected from the group consisting of a tissue sample, a whole blood sample, a serum sample, and a plasma sample. More specifically, the sample is a tissue sample, notably a fixed tissue sample. In some instances, the tissue sample is a tumor sample.

The present disclosure yet further provides for the use of a Nectin-4 antibody in the manufacture of a reagent for use in a method of diagnosing a subject suffering from a disorder (e.g., a cancer), the method comprising: determining the presence or expression level of Nectin-4 in a sample obtained from the subject by contacting the sample with an anti-Nectin-4 antibody as herein disclosed and detecting the presence of the bound antibody. In some embodiments, the sample is selected from the group consisting of a tissue sample, a whole blood sample, a serum sample, and a plasma sample. More specifically, the sample is a tissue sample, notably a fixed tissue sample. In some instances, the tissue sample is a tumor sample.

In another embodiment, the present disclosure provides a method for identifying a subject suffering from a disorder (e.g., cancer) who is likely to respond to a treatment, the method including: determining the presence or expression level of Nectin-4 in a sample obtained from the subject by contacting the sample with an anti-Nectin-4 antibody as herein disclosed and detecting the presence of the bound antibody, wherein the presence or expression level of Nectin-4 in the sample indicates that the subject is likely to respond to the treatment.

In one embodiment, the present disclosure also provides a method for predicting responsiveness of an individual suffering from a cancer to treatment with an anti-cancer therapy. Typically the anti-cancer therapy comprised an anti-Nectin-4 antibody as herein described (for example conjugated to a cytotoxic moitie), or a chimeric antigen receptor (CAR) as previously herein defined. The method comprises: determining the presence or expression level of Nectin-4 in a sample obtained from the subject by contacting the sample with an anti-Nectin-4 antibody as herein disclosed and detecting the presence of the bound antibody, wherein the presence or expression level of Nectin-4 in the sample indicates that the subject is more likely to respond to treatment with the anti-cancer therapy. In some embodiments, the sample is selected from the group consisting of a tissue sample, a whole blood sample, a serum sample, and a plasma sample. More specifically, the sample is a tissue sample, notably a fixed tissue sample. In some instances, the tissue sample is a tumor sample.

The present disclosure also encompasses a method for monitoring a treatment efficacy in a patient receiving an anti-Nectin-4 antibody, or a CAR as herein defined. Said method comprises determining in a biological sample of the patient at two or more time points the nectin-4 protein level of expression (or Nectin-4 concentration). Measurement of a higher nectin-4 protein level of expression (typically assessed by determining nectin-4 concentration in said biological sample) in a biological sample of the patient at a later time point, compared to a value obtained in a biological sample of the patient at an earlier time point (thus typically used as a reference value), is indicative that the patient is non-responder to the treatment. Measurement of a lower nectin-4 protein level expression (or nectin-4 concentration) is indicative that the patient is responder to the treatment. Measurement of an equal nectin-4 protein level (or nectin-4 concentration) at the two or more times points indicates that the nectin-4 associated disease, typically the cancer, does not progress (i.e., is stable) in the patient.

More specifically in embodiments of the present disclosure as previously described, the presence and/or expression level/amount of Nectin-4 in a sample may be determined using IHC and staining protocols using an anti-Nectin-4 antibody of the present disclosure. ITC staining of tissue sections has been shown to be a reliable method of determining or detecting the presence of proteins in a sample. In one embodiment, expression level of Nectin-4 is determined using a method comprising: (a) performing IHC analysis of a sample (such as a tumor sample obtained from a subject) with an anti-Nectin-4 antibody as herein disclosed; and (b) determining the presence and/or expression level of Nectin-4 in the sample. In some embodiments, IHC staining intensity is determined relative to a reference. In some embodiments, the reference is a reference value. In some embodiments, the reference is a reference sample (e.g., a control cell line staining sample, a tissue sample from non-cancerous patient, a reference sample known to have a pre-determined level of Nectin-4 expression IHC may be performed in combination with additional techniques such as morphological staining and/or in situ hybridization (e.g., FISH). Two general methods of IHC are available: direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically can be labeled with a detectable moiety. Numerous labels are available which can be generally grouped into the following categories: (a) radioisotopes, such as $^{15}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl^-D-galactosidase) or fluorogenic substrate (e.g., 4-methylumbelliferyl-D-galactosidase). For a general review of these, see, for example, U.S. Pat. Nos. 4,275,149 and 4,318,980.

As previously mentioned, in the serum of cancer patients, notably patients suffering from breast cancer, the detection of soluble forms of Nectin-4 is associated with a poor prognosis. Furthermore, it has been shown that the level of Nectin-4 increases with metastasis progression and decreases after treatment (Ref 1). Thus, in some embodiments, the present disclosure encompasses a method for the prognosis of the clinical outcome of a subject suffering from a cancer. Said method comprises a step of determining the presence or the expression level of Nectin-4 in a sample obtained from the subject by contacting the sample with an anti-Nectin-4 antibody as previously herein described and detecting the presence of the bound antibody. Typically, the detection of Nectin 4 and/or the detection of an expression level of Nectin-4 in said sample above a reference level is indicative of a poor prognosis. Alternatively, the absence of Nectin-4 in the sample or the detection of a level of Nectin-4 below a reference value is indicative of a good prognosis.

The present disclosure further encompasses a method for the treatment of cancer comprising (i) a diagnosing step as above defined and, (ii) if Nectin-4 is detected and/or if the level of Nectin-4 is greater or equal to a reference value, a step of administering an antibody or as previously defined, notably conjugated to a cytotoxic moiety, and/or administering a chimeric antigen receptor or a composition comprising thereof as defined above.

In particular, the present disclosure encompasses a method of treatment of a patient suffering from or suspected of suffering from a cancer comprising:
- a step 1) of assessing Nectin-4 expression in a tissue sample from a subject suspected of having cancer, or of assessing responsiveness of said cancer patient to an anti-cancer therapeutic agent comprising:
  - (1a) contacting said tissue sample with the antibody or antigen binding fragment thereof as herein disclosed;
  - (1b) detecting the binding of said antibody or antigen binding fragment thereof to said tissue sample; and
  - (1c) determining the expression of Nectin-4 in the tissue sample, wherein the expression level of Nectin-4 in the tissue sample is compared with a reference expression level of Nectin-4; and
- a step 2) of administering said anti-cancer therapeutic agent to the patient when an increased expression level of Nectin-4 compared to the reference is observed;
- optionally wherein, the expression level of Nectin-4 is detected using an immunohistochemistry (IHC) approach, an immunoblotting assay, a fluorescence activated cell sorting (FACS) assay, or an Enzyme-Linked Immunosorbent Assay (ELISA),
- optionally wherein, the anti-cancer therapeutic agent comprises an anti-Nectin-4 antibody or an antibody drug conjugate of an anti-Nectin-4 antibody, typically of an antibody according to the present disclosure or a variant thereof.

In the methods above, the reference value may be chosen as above defined. Sample(s) as herein defined can also be obtained as previously described. The term cancer as herein intended as been previously defined, notably in the present section.

The present disclosure will be further illustrated by the following figures and examples. However, these examples and figures should not be interpreted in any way as limiting the scope of the present disclosure.

TABLE 1

Sequences of the present disclosure: CDRs in the table below are numbered according to the IMGT nomenclature.

| Description of the sequence | type | SEQ ID NO: | sequence |
|---|---|---|---|
| Nectin 4 | aa | 1 | MPLSLGAEMWGPEAWLLLLLLLASFTGRCPAGEL ETSDVVTVVLGQDAKLPCFYRGDSGEQVGQVAW ARVDAGEGAQELALLHSKYGLHVSPAYEGRVEQP PPPRNPLDGSVLLRNAVQADEGEYECRVSTFPAGS FQARLRLRVLVPPLPSLNPGPALEEGQGLTLAASCT AEGSPAPSVTWDTEVKGTTSSRSFKHSRSAAVTSE FHLVPSRSMNGQPLTCVVSHPGLLQDQRITHILHVS FLAEASVRGLEDQNLWHIGREGAMLKCLSEGQPPP SYNWTRLDGPLPSGVRVDGDTLGFPPLTTEHSGIY VCHVSNEFSSRDSQVTVDVLDPQEDSGKQVDLVS ASVVVVGVIAALLFCLLVVVVLMSRYHRRKAQQ MTQKYEEELTLTRENSIRRLHSHHTDPRSQPEESVG LRAEGHPDSLKDNSSCSVMSEEPEGRSYSTLTTVR EIETQTELLSPGSGRAEEEEDQDEGIKQAMNHFVQ ENGTLRAKPTGNGIYINGRGHLV |
| HCDR1 mAb 5A12.2 | aa | 2 | GFTFNSMY |
| HCDR2 mAb 5A12.2 | aa | 3 | IYAGTGGT |
| HCDR3 mAb 5A12.2 | aa | 4 | AIRSGFVPMDYWG |
| LCDR1 mAb 5A12.2 | aa | 5 | QSVSND |
| LCDR2 mAb 5A12.2 | aa | 6 | YAS |
| LCDR3 mAb 5A12.2 | aa | 7 | QQDYSS |
| VH (variable heavy chain) | aa | 8 | QIQLQQSGAELVKPGASVTLSCKTSGFTFNSMYIS WLKQKPGQSLEWIAWIYAGTGGTRFNQKFTGKV |

TABLE 1-continued

Sequences of the present disclosure:
CDRs in the table below are numbered according to the
IMGT nomenclature.

| Description of the sequence | type | SEQ ID NO: | sequence |
|---|---|---|---|
| mAb 5A12.2 (with HCDRs in bold) | | | QLTVDTSSSTAYMQFSSLTTDDSAIYYCAIRSGFVP MDYWGQGTSVTVSS |
| VL (variable light kappa chain) mAb 5A12.2 (with LCDRs in bold) | aa | 9 | SIVMTQTPKFLLVSAGDRVTITCKASQSVSNDVAW YQQKPGQSPKLLIYYASNRYTGVPDRFTGSGYGTD FTFTISTVQAEDLAVYFCQQDYSSPWTFGGGTKLEI K |
| VH (variable heavy chain) mAb 5A12.2 (with HCDRs in bold) | nt | 10 | CAGATCCAGCTGCAGCAGTCTGGAGCTGAGCTG GTGAAGCCTGGGGCTTCAGTGACGCTGTCCTGCA AGACTTCTGGCTTCACCTTCAACAGTATGTATAT AAGTTGGTTGAAGCAAAAGCCTGGACAGAGTCT TGAGTGGATTGCATGGATTTATGCTGGAACTGGT GGTACTAGGTTTAATCAGAAGTTCACAGGCAAG GTCCAACTGACTGTAGACACATCCTCCAGCACA GCCTACATGCAATTCAGCCTGACAACTGAC GACTCTGCCATCTATTACTGTGCCATCAGGTCGG GCTTCGTCCCTATGGACTACTGGGGTCAAGGGAC CTCAGTCACCGTCTCCTCA |
| VL (variable light kappa chain) mAb 5A12.2 (with LCDRs in bold) | nt | 11 | AGTATTGTGATGACCCAGACTCCCAAATTCCTGC TTGTATCAGCAGGAGACAGGGTTACCATAACCT GCAAGGCCAGTCAGAGTGTGAGTAATGATGTAG CTTGGTACCAACAGAAGCCAGGACAGTCTCCTA AACTCCTGATATACTATGCATCCAATCGCTACAC TGGAGTCCCTGATCGCTTCACTGGCAGTGGATAT GGGACGGATTTCACTTTCACCATCAGCACTGTGC AGGCTGAAGACCTGGCAGTTTATTTCTGTCAGCA GGATTATAGCTCTCCGTGGACGTTCGGTGGAGGC ACCAAGCTGGAAATCAAA |

LEGENDS OF THE FIGURES

FIG. 1: Competition Assay for 5A12.2 Binding to Nectin-4.

A: Binding of 5A12.2-HRP mAb on recombinant nectin-4 protein was performed by ELISA in the presence of variable concentration of other nectin-4 mAbs. No cross inhibition is detected.

B: Table summarizing competition between anti-nectin-4 mAbs. Black: mab competition. Gray: no mAb competition. 5A12.2 epitope differs from N41mAb, 14A5.2 and Ha22.2

FIG. 2: Determination of the Apparent Affinity-Binding Constant ($K_D$) Values:

MAbs were tested for binding to cell surface nectin-4 expressed by SUM190 tumor cells. Apparent affinity-binding constant ($K_D$) was calculated using Graph Pad Prism software. F-Max value corresponds to the maximum fluorescence intensity (a.u.) measured by FACS analysis.

Figure 3:
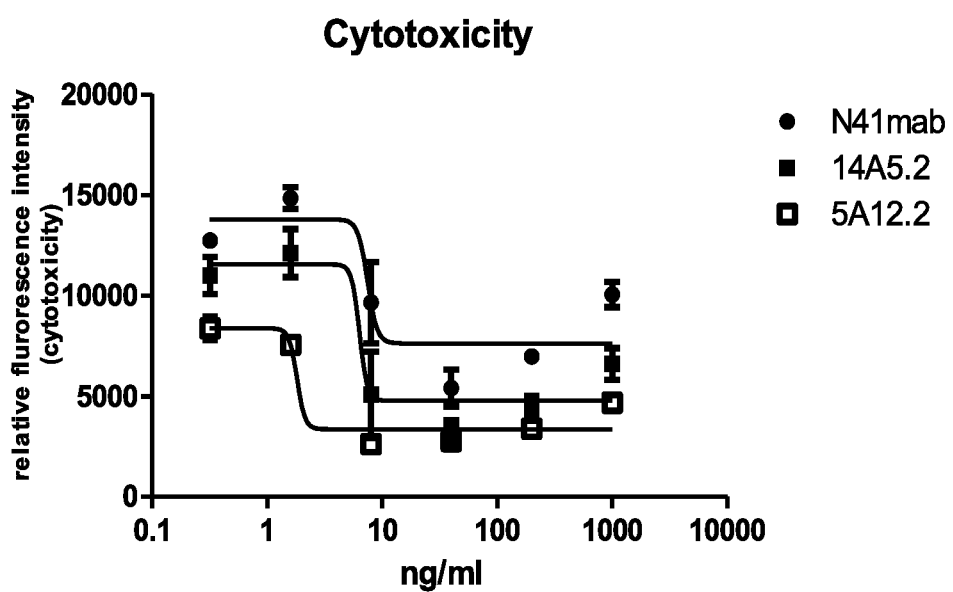

FIG. 3: Cell Cytotoxicity Analysis:

ADC capacity of anti-nectin-4 mAbs was evaluated using the mab-ZAP kit from ATS-bio on the SUM190 tumor cell line. IC50 were calculated using the Graph Pad Prism software.

Figure 4:
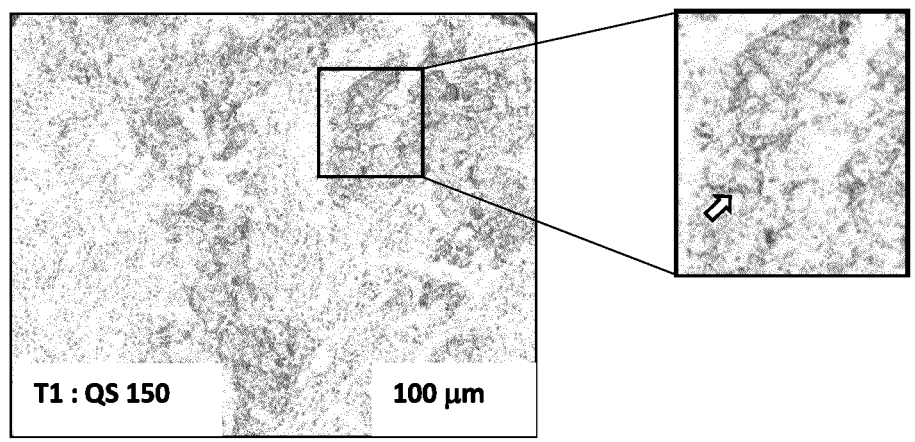
Figure 4:
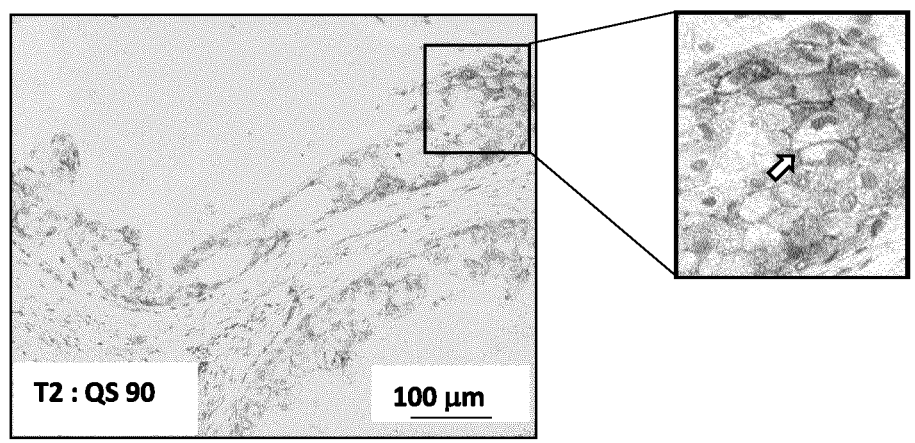

FIG. 4: IHC Staining of Nectin-4 in Primary Triple-Negative Breast Cancer Patient Samples:

FFPE tissues were stained with the 5A12.2 mAb as described in material and methods. Nectin-4 expression was scored (Quick score, QS) by multiplying the percentage of positive cells (P) by the intensity (I). Formula: QS=P×I. Maximum score is 300. Left; T1: Patient tumor 1, T2: Patient tumor 2. Right: zoom highlighting membranous expression (arrow) of nectin-4 as expected.

EXAMPLES

Material and Methods

Selection of 5A12.2 Hybridoma

Balb/C mice were immunized with recombinant human Nectin-4-Fc protein as immunogen. This protein consists in the IgV distal domain of the extracellular region of Nectin-4. The immune splenocytes were fused to the murine X63Ag8.653 myeloma cells. Hybridoma supernatants (~2000) were screened by FACS on Nectin-4 transfected vs non transfected cells. Hybridoma producing Nectin-4 antibodies were further screened for affinity, fluorescence intensity and compared to previous Nectin-4 antibodies. The 5A12.2 was selected as an antibody with improved characteristics.

Competition Assay

Mab competition assay was performed by ELISA. Ninety-six-well trays were coated with 0.125 µg/ml of recombinant nectin4VCC-Fc protein overnight at +4° C. Binding of peroxidase conjugated 5A12.2 mAb (5A12.2-HRP at 0.55 µg/ml) was measured in the presence of variable concentration of 4 different anti-nectin-4 mAbs (5A12, N41, 14A5 and Ha22-2 mabs).

Flow Cytometry:

FACS analysis was performed on SUM190 breast cancer cell line using indicated concentration of nectin-4 monoclonal antibodies. Cells were then stained with phycoerythrin conjugate goat anti mouse antibody (Beckman-Coulter).

Apparent Affinity-Binding Constant ($K_D$) Values and Maximum Fluorescence Intensity Determination:

$K_D$ values were defined by FACS analysis using serial dilutions of monoclonal antibodies. Graph Pad Prism software was used for accurate measurements. Maximum fluorescence intensity was measured by FACS analysis.

ADC-Based Targeting of Nectin-4 In Vitro

Anti-nectin-4 monoclonal antibodies were tested for their capacity to induce ADC-based cytotoxicity on SUM190 tumor cells. Experiments were done by incubating 3000 cells/well in triplicate with serial dilutions of antibodies and with a goat anti-mouse monoclonal antibody conjugated to saporin as recommended by the manufacturer (mab-ZAP kit, ATS-bio). To analyse the effect, cell growth was measured using the alamarBlue staining procedure as recommended by the manufacturer (Biosource, CA, USA). The test incorporates a fluorescent oxidation-reduction indicator. Fluorescence intensity is proportional to cellular metabolic reduction. AlamarBlue was measured at day 5 by incubating 1/10 volume of alamarBlue solution for 2 h at 37° C. and read at 595 nm (FLUOstar Optima, BMG Labtech).

IHC Staining on FFPE Breast Cancer Samples

Samples were fixed for 24 to 48 in 4% formaldehyde. Discovery HQ procedure was used: Antigen retrieval at pH8.0 was performed for 12 min at 95° C. 5A12 mAb was used at 1 µg/ml and incubated 3 h at 37° C. Experiment was done with the Discovery XT Ventana from Roche. Detection of staining was done using the Discovery Anti-Mouse HQ, the Discovery Anti-HQ and the Chromomap DAB as recommended by the manufacturer (Roche Diagnostics).

RESULTS

The present results disclose a new anti-nectin-4 mAb with improved properties. This mAb named 5A12.2 recognizes IgV-like distal domain in the extracellular region of nectin-4. Their binding properties were compared, in terms of epitope recognition, with other already patented mabs. (PCT/EP2018/055109 and PCT/EP2106/071076)

As seen in FIGS. 1A and B, 5A12.2 mab recognized an epitope that differs from the three other tested mAbs, i.e., N41, 14A5.2 and Ha22.2. FACS analysis shows that the 5A12.2 mAb exhibits better apparent affinity compared to N41 and 14A5 mAbs (FIG. 2, top). Interestingly, the 5A12.2 mAb max binding affinity is higher compared to the two other mAbs (FIG. 2, bottom).

These properties led the inventors to compare ADC properties of this mab. As seen in FIG. 3 top, the 5A12.2 mAb is cytotoxic when conjugated to the toxin saporin (a highly potent inhibitor of ribosomal functions). Cytotoxicity is higher than for the N41 and the 14A5 mAbs (FIG. 3, bottom).

At last, IHC experiments have been carried out to evaluate the properties of the 5A12.2 mAb to recognize and stain paraffin embedded tissues. As shown in FIG. 4, nectin-4 expression in breast cancer tissues were readily detected as membranous staining as expected. This is, to the inventor's knowledge, the first anti-nectin-4 mAb that works on FFPE tissues. Thus, the 5A12.2 mAb represents a new alternative for the diagnosis, prognosis and treatment of nectin-4 positive tumors.

REFERENCES

1. Fabre-Lafay S et al. Nectin-4 is a new histological and serological tumor associated marker for breast cancer. BMC Cancer 2007; 7: 73.
2. Takano A et al. Identification of nectin-4 oncoprotein as a diagnostic and therapeutic target for lung cancer. Cancer Res 2009; 69: 6694-6703.
3. Derycke M S et al. Nectin 4 overexpression in ovarian cancer tissues and serum: potential role as a serum biomarker. Am J ClinPathol 2010; 134: 835-845.
4. Nishiwada S et al. Nectin-4 expression contributes to tumor proliferation, angiogenesis and patient prognosis in human pancreatic cancer. J Exp Clin Cancer Res 2015; 34: 30.
5. Challita-Eid P M et al. EnfortumabVedotin Antibody-Drug Conjugate Targeting Nectin-4 Is a Highly Potent Therapeutic Agent in Multiple Preclinical Cancer Models. Cancer Res 2016; 76: 3003-3013.
6. M-Rabet et al. Nectin-4: a new prognostic biomarker for efficient therapeutic targeting of primary and metastatic triple-negative breast cancer. Ann Oncol. 2017 Apr. 1; 28(4):769-776
7. Fabre S et al., Prominent role of the Ig-like V domain in trans-interactions of nectins. Nectin-3 and nectin-4 bind to the predicted C- C'-C"-D beta-strands of the nectin-1 V domain. J Biol Chem. 2002 Jul. 26; 277(30):27006-13.

The invention claimed is:

1. An antibody having specificity for human Nectin-4 and comprising a HCDR1 comprising SEQ ID NO:2, a HCDR2 comprising SEQ ID NO:3, a HCDR3 comprising SEQ ID NO:4, a LCDR1 comprising SEQ ID NO:5, a LCDR2 comprising SEQ ID NO:6 and a LCDR3 comprising SEQ ID NO:7.

2. The anti-Nectin-4 antibody according to claim 1, which is a chimeric or humanized antibody.

3. A nucleic acid molecule, which encodes a heavy chain and a light chain of the anti-Nectin-4 antibody of claim 1.

4. A host cell comprising the nucleic acid molecule according to claim 3.

5. A method of treating cancer in a subject in need thereof, comprising administering a therapeutically effective amount of an anti-Nectin-4 antibody according to claim 1.

6. The method according to claim 5, wherein the cancer is breast cancer, ovarian cancer, bladder cancer, urothelial cancer, pancreatic cancer or lung cancer.

7. The method according to claim 5, wherein the cancer is metastatic cancer.

8. A pharmaceutical composition comprising an anti-Nectin-4 antibody according to claim 1, and at least a pharmaceutically acceptable carrier.

9. A method for detecting the presence or expression level of Nectin-4 in a biological sample, wherein the step of detecting is performed by using an anti-Nectin-4 antibody according to claim 1 in an immunohistochemistry (IHC) assay.

10. The method according to claim 9, wherein the biological sample is a fixed tissue sample.

11. The method according to claim 10, wherein the biological sample is a formalin-fixed paraffin-embedded (FFPE) tissue.

12. A method of treating a subject suffering from cancer characterized by expression of Nectin-4, the method comprising 1) detecting the expression of Nectin-4 in a tissue sample from the subject in comparison to a reference expression level of Nectin-4 by:
   (1a) contacting a tissue sample from the subject with the antibody of claim 1 or an antigen binding fragment thereof; and
   (1b) detecting binding of the antibody or antigen binding fragment to the tissue sample; and
2) administering an anti-cancer therapeutic agent to the subject when an increased expression level of Nectin-4 compared to the reference expression level of Nectin-4 is observed.

13. The method according to claim 12, wherein the expression level of Nectin-4 is detected using an immunohistochemistry (IHC) approach, an immunoblotting assay, a fluorescence activated cell sorting (FACS) assay, or an Enzyme-Linked Immunosorbent Assay (ELISA).

14. The antibody of claim 1 characterized in that it has one of the following functions:
   i. the antibody binds to the human Nectin-4 of SEQ ID NO:1 with a $K_D$ of less than 10 µg/mL; and
   ii. the antibody selectively binds to Nectin-4 in a biological sample in an immunohistochemistry (IHC) assay.

15. The antibody of claim 1 characterized in that it has both of the following functions:
   i. the antibody binds to the human Nectin-4 of SEQ ID NO:1 with a $K_D$ of less than 10 µg/mL; and
   ii. the antibody selectively binds to Nectin-4 in a biological sample in an immunohistochemistry (IHC) assay.

16. The anti-Nectin-4 antibody of claim 1, which comprises a variable heavy chain (VH) domain and a variable light chain domain having at least 90% identity with the heavy chain and light chain comprising SEQ ID NO:8 and 9 respectively.

17. The anti-Nectin-4 antibody of claim 1, which comprises a variable heavy chain (VH) domain and a variable light chain comprising SEQ ID NO:8 and 9 respectively.

18. One nucleic acid molecule, which encodes a heavy chain of the anti-Nectin-4 antibody of claim 1 or a light chain of the anti-Nectin-4 antibody of claim 1.

19. A host cell comprising the nucleic acid molecule according to claim 18.

20. A method of treating a subject suffering from cancer characterized by expression of Nectin-4, the method comprising administering the antibody of claim 1 to the subject.

* * * * *

SEQUENCE LISTING

```
<160> NUMBER OF SEQ ID NOS: 11

<210> SEQ ID NO 1
<211> LENGTH: 510
<212> TYPE: PRT
<213> ORGANISM: Homo sapiens

<400> SEQUENCE: 1

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
```

-continued

```
                65                  70                  75                  80
Leu Leu His Ser Lys Tyr Gly Leu His Val Ser Pro Ala Tyr Glu Gly
                    85                  90                  95
Arg Val Glu Gln Pro Pro Pro Arg Asn Pro Leu Asp Gly Ser Val
                100                 105                 110
Leu Leu Arg Asn Ala Val Gln Ala Asp Glu Gly Glu Tyr Glu Cys Arg
                115                 120                 125
Val Ser Thr Phe Pro Ala Gly Ser Phe Gln Ala Arg Leu Arg Leu Arg
                130                 135                 140
Val Leu Val Pro Pro Leu Pro Ser Leu Asn Pro Gly Pro Ala Leu Glu
145                 150                 155                 160
Glu Gly Gln Gly Leu Thr Leu Ala Ala Ser Cys Thr Ala Glu Gly Ser
                    165                 170                 175
Pro Ala Pro Ser Val Thr Trp Asp Thr Glu Val Lys Gly Thr Thr Ser
                180                 185                 190
Ser Arg Ser Phe Lys His Ser Arg Ser Ala Ala Val Thr Ser Glu Phe
                195                 200                 205
His Leu Val Pro Ser Arg Ser Met Asn Gly Gln Pro Leu Thr Cys Val
                210                 215                 220
Val Ser His Pro Gly Leu Leu Gln Asp Gln Arg Ile Thr His Ile Leu
225                 230                 235                 240
His Val Ser Phe Leu Ala Glu Ala Ser Val Arg Gly Leu Glu Asp Gln
                245                 250                 255
Asn Leu Trp His Ile Gly Arg Glu Gly Ala Met Leu Lys Cys Leu Ser
                260                 265                 270
Glu Gly Gln Pro Pro Pro Ser Tyr Asn Trp Thr Arg Leu Asp Gly Pro
                275                 280                 285
Leu Pro Ser Gly Val Arg Val Asp Gly Asp Thr Leu Gly Phe Pro Pro
                290                 295                 300
Leu Thr Thr Glu His Ser Gly Ile Tyr Val Cys His Val Ser Asn Glu
305                 310                 315                 320
Phe Ser Ser Arg Asp Ser Gln Val Thr Val Asp Val Leu Asp Pro Gln
                325                 330                 335
Glu Asp Ser Gly Lys Gln Val Asp Leu Val Ser Ala Ser Val Val Val
                340                 345                 350
Val Gly Val Ile Ala Ala Leu Leu Phe Cys Leu Leu Val Val Val Val
                355                 360                 365
Val Leu Met Ser Arg Tyr His Arg Arg Lys Ala Gln Gln Met Thr Gln
                370                 375                 380
Lys Tyr Glu Glu Glu Leu Thr Leu Thr Arg Glu Asn Ser Ile Arg Arg
385                 390                 395                 400
Leu His Ser His His Thr Asp Pro Arg Ser Gln Pro Glu Glu Ser Val
                    405                 410                 415
Gly Leu Arg Ala Glu Gly His Pro Asp Ser Leu Lys Asp Asn Ser Ser
                420                 425                 430
Cys Ser Val Met Ser Glu Glu Pro Glu Gly Arg Ser Tyr Ser Thr Leu
                435                 440                 445
Thr Thr Val Arg Glu Ile Glu Thr Gln Thr Glu Leu Leu Ser Pro Gly
                450                 455                 460
Ser Gly Arg Ala Glu Glu Glu Asp Gln Asp Glu Gly Ile Lys Gln
465                 470                 475                 480
Ala Met Asn His Phe Val Gln Glu Asn Gly Thr Leu Arg Ala Lys Pro
                    485                 490                 495
```

```
Thr Gly Asn Gly Ile Tyr Ile Asn Gly Arg Gly His Leu Val
            500                 505                 510

<210> SEQ ID NO 2
<211> LENGTH: 8
<212> TYPE: PRT
<213> ORGANISM: Artificial Sequence
<220> FEATURE:
<223> OTHER INFORMATION: Synthetic HCDR1 mAb 5A12.2

<400> SEQUENCE: 2

Gly Phe Thr Phe Asn Ser Met Tyr
1               5

<210> SEQ ID NO 3
<211> LENGTH: 8
<212> TYPE: PRT
<213> ORGANISM: artificial sequence
<220> FEATURE:
<223> OTHER INFORMATION: Synthetic HCDR2 mAb 5A12.2

<400> SEQUENCE: 3

Ile Tyr Ala Gly Thr Gly Gly Thr
1               5

<210> SEQ ID NO 4
<211> LENGTH: 13
<212> TYPE: PRT
<213> ORGANISM: artificial sequence
<220> FEATURE:
<223> OTHER INFORMATION: Synthetic HCDR3 mAb 5A12.2

<400> SEQUENCE: 4

Ala Ile Arg Ser Gly Phe Val Pro Met Asp Tyr Trp Gly
1               5                   10

<210> SEQ ID NO 5
<211> LENGTH: 6
<212> TYPE: PRT
<213> ORGANISM: artificial sequence
<220> FEATURE:
<223> OTHER INFORMATION: Synthetic LCDR1 mAb 5A12.2

<400> SEQUENCE: 5

Gln Ser Val Ser Asn Asp
1               5

<210> SEQ ID NO 6
<211> LENGTH: 3
<212> TYPE: PRT
<213> ORGANISM: artificial sequence
<220> FEATURE:
<223> OTHER INFORMATION: Synthetic LCDR2 mAb 5A12.2

<400> SEQUENCE: 6

Tyr Ala Ser
1

<210> SEQ ID NO 7
<211> LENGTH: 6
<212> TYPE: PRT
<213> ORGANISM: artificial sequence
<220> FEATURE:
<223> OTHER INFORMATION: Synthetic LCDR3 mAb 5A12.2

<400> SEQUENCE: 7
```

Gln Gln Asp Tyr Ser Ser
1               5

<210> SEQ ID NO 8
<211> LENGTH: 118
<212> TYPE: PRT
<213> ORGANISM: artificial sequence
<220> FEATURE:
<223> OTHER INFORMATION: Synthetic VH mAb 5A12.2

<400> SEQUENCE: 8

Gln Ile Gln Leu Gln Gln Ser Gly Ala Glu Leu Val Lys Pro Gly Ala
1               5                   10                  15

Ser Val Thr Leu Ser Cys Lys Thr Ser Gly Phe Thr Phe Asn Ser Met
                20                  25                  30

Tyr Ile Ser Trp Leu Lys Gln Lys Pro Gly Gln Ser Leu Glu Trp Ile
            35                  40                  45

Ala Trp Ile Tyr Ala Gly Thr Gly Thr Arg Phe Asn Gln Lys Phe
        50                  55                  60

Thr Gly Lys Val Gln Leu Thr Val Asp Thr Ser Ser Ser Thr Ala Tyr
65                  70                  75                  80

Met Gln Phe Ser Ser Leu Thr Thr Asp Asp Ser Ala Ile Tyr Tyr Cys
                85                  90                  95

Ala Ile Arg Ser Gly Phe Val Pro Met Asp Tyr Trp Gly Gln Gly Thr
            100                 105                 110

Ser Val Thr Val Ser Ser
        115

<210> SEQ ID NO 9
<211> LENGTH: 107
<212> TYPE: PRT
<213> ORGANISM: artificial sequence
<220> FEATURE:
<223> OTHER INFORMATION: Synthetic VL mAb 5A12.2

<400> SEQUENCE: 9

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 10
<211> LENGTH: 354
<212> TYPE: DNA
<213> ORGANISM: artificial sequence
<220> FEATURE:
<223> OTHER INFORMATION: Synthetic VH mAb 5A12.2

<400> SEQUENCE: 10
cagatccagc tgcagcagtc tggagctgag ctggtgaagc ctggggcttc agtgacgctg        60

```
tcctgcaaga cttctggctt caccttcaac agtatgtata taagttggtt gaagcaaaag    120
cctggacaga gtcttgagtg gattgcatgg atttatgctg gaactggtgg tactaggttt    180
aatcagaagt tcacaggcaa ggtccaactg actgtagaca catcctccag cacagcctac    240
atgcaattca gcagcctgac aactgacgac tctgccatct attactgtgc catcaggtcg    300
ggcttcgtcc ctatggacta ctggggtcaa gggacctcag tcaccgtctc ctca          354

<210> SEQ ID NO 11
<211> LENGTH: 321
<212> TYPE: DNA
<213> ORGANISM: artificial sequence
<220> FEATURE:
<223> OTHER INFORMATION: Synthetic VL mAb 5A12.2

<400> SEQUENCE: 11
agtattgtga tgacccagac tcccaaattc ctgcttgtat cagcaggaga cagggttacc     60
ataacctgca aggccagtca gagtgtgagt aatgatgtag cttggtacca acagaagcca    120
ggacagtctc ctaaactcct gatatactat gcatccaatc gctacactgg agtccctgat    180
cgcttcactg gcagtggata tgggacggat ttcactttca ccatcagcac tgtgcaggct    240
gaagacctgg cagtttattt ctgtcagcag gattatagct ctccgtggac gttcggtgga    300
ggcaccaagc tggaaatcaa a                                              321
```